United States Patent
Bertani et al.

(10) Patent No.: US 8,030,322 B2
(45) Date of Patent: Oct. 4, 2011

(54) SPIROCOMPOUNDS USEFUL AS MODULATORS FOR DOPAMINE D3 RECEPTORS

(75) Inventors: Barbara Bertani, Verona (IT); Romano Di Fabio, Verona (IT); Fabrizio Micheli, Verona (IT); Alessandra Pasquarello, Verona (IT); Luca Tarsi, Verona (IT); Silvia Terreni, Verona (IT)

(73) Assignee: Glaxo Group Limited, Greenford, Middlesex (GB)

( * ) Notice: Subject to any disclaimer, the term of this patent is extended or adjusted under 35 U.S.C. 154(b) by 123 days.

(21) Appl. No.: 12/297,253

(22) PCT Filed: Apr. 24, 2007

(86) PCT No.: PCT/EP2007/054003
§ 371 (c)(1),
(2), (4) Date: May 26, 2009

(87) PCT Pub. No.: WO2007/125061
PCT Pub. Date: Nov. 8, 2007

(65) Prior Publication Data
US 2010/0063078 A1    Mar. 11, 2010

(30) Foreign Application Priority Data

Apr. 27, 2006 (GB) .................................. 0608452.9
Apr. 27, 2006 (GB) .................................. 0608457.8

(51) Int. Cl.
*C07D 403/06* (2006.01)
*C07D 409/14* (2006.01)
*A61K 31/421* (2006.01)
*A61K 31/506* (2006.01)

(52) U.S. Cl. ........ 514/274; 514/337; 514/338; 514/339; 514/365; 514/374; 544/310; 544/311; 544/312; 548/181; 548/235

(58) Field of Classification Search .................. 544/310, 544/311, 312; 548/181, 235; 514/274, 365, 514/374
See application file for complete search history.

(56) References Cited

FOREIGN PATENT DOCUMENTS
DK    43 38 396    5/1995

OTHER PUBLICATIONS

Le Foll et al., PubMed Abstract (Expert Opinion Investig Drugs, 16(1):45-57), Jan. 2007.*
Layzer, Degenerative Diseases of the Nervous System, Cecil Textbook of Medicine, 20th Edition, vol. 2, pp. 2050-2057, 1996.*
Damasio, Alzheimer's Disease and Related Dementias, Cecil Textbook of Medicine, 20th Edition, vol. 2, pp. 1992-1996, 1996.*
Rice, M.L. et al: "Spirans. XVII. Spirans derived from 4-chromanone" Journal of Heterocyclic Chemistry, Provo, UT, US. vol. 8, No. 1, 1971, pp. 155-156.

* cited by examiner

*Primary Examiner* — Deepak Rao
(74) *Attorney, Agent, or Firm* — Bonnie L. Deppenbrock

(57) ABSTRACT

The present invention relates to compounds of formula (I) or salts thereof

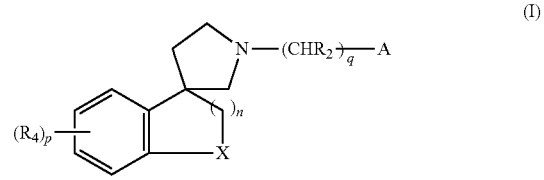

wherein A, X, $R_2$, $R_4$ and n are defined herein, processes for their preparation, intermediates used in these processes, pharmaceutical compositions containing them and their use in therapy, as modulators of dopamine $D_3$ receptors, e.g., to treat drug dependency, as antipsychotic agents, to treat obsessive compulsive spectrum disorders, premature ejaculation or to enhance cognition.

5 Claims, No Drawings

SPIROCOMPOUNDS USEFUL AS MODULATORS FOR DOPAMINE D3 RECEPTORS

This application is a 371 of International Application No. PCT/EP2007/054003 filed 24 Apr. 2007, this application claims the priority of GB 0608452.9 filed 27 Apr. 2006 and GB 0608457.8 filed 27 Apr. 2006 which are incorporated herein in their entirety.

The present invention relates to novel compounds, processes for their preparation, intermediates used in these processes, pharmaceutical compositions containing them and their use in therapy, as modulators of dopamine $D_3$ receptors.

A new class of compounds which have affinity for dopamine receptors, in particular the dopamine $D_3$ receptor has been found. These compounds have potential in the treatment of conditions wherein modulation of the $D_3$ receptor is beneficial.

The present invention provides compounds of formula (I) or salts thereof:

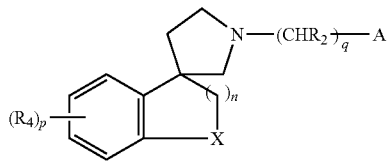

(I)

wherein

A is a substituent selected in the group consisting of P, P1, P2 and P3 wherein

P is

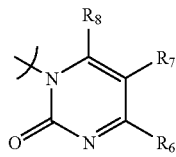

P1 is

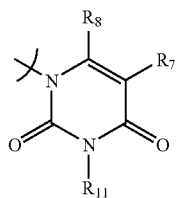

P2 is

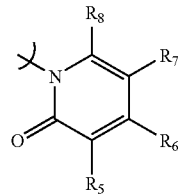

P3 is

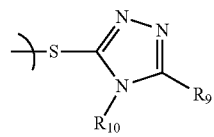

p is an integer ranging from 0 to 4;
$R_4$ is selected in the group consisting of halogen, hydroxy, cyano, $C_{1-4}$ alkyl, halo$C_{1-4}$alkyl, $C_{1-4}$ alkoxy, halo$C_{1-4}$ alkoxy, $C_{1-4}$alkanoyl, $SF_5$ and a 5- or 6-membered monocyclic heteroaryl group; and when p is an integer ranging from 2 to 4, each $R_4$ may be the same or different;
$R_2$ is hydrogen or $C_{1-4}$alkyl;
q is 3, 4 or 5;
n is 0, 1 or 2;
X is $CR_1R_3$— or —O—;
$R_1$ is selected in the group consisting of hydrogen, $C_{1-4}$ alkyl and fluorine;
$R_3$ is selected in the group consisting of hydrogen, $C_{1-4}$alkyl and fluorine;
$R_5$ is selected in the group consisting of: hydrogen, halogen, hydroxy, cyano, $C_{1-4}$alkyl, $C_{3-7}$ cycloalkyl, halo$C_{1-4}$ alkyl, $C_{1-4}$alkoxy, halo$C_{1-4}$alkoxy, $C_{1-4}$ alkanoyl and NR'R"; or $R_5$ is a phenyl group, a 5-14 membered heterocyclic group; and any of such phenyl or heterocyclic group is optionally substituted by 1, 2, 3 or 4 substituents selected from the group consisting of: halogen, cyano, $C_{1-4}$alkyl, halo$C_{1-4}$alkyl, $C_{1-4}$ alkoxy, $C_{1-4}$alkanoyl and $SF_5$;
$R_6$ is selected in the group consisting of: hydrogen, halogen, hydroxy, cyano, $C_{3-7}$ cycloalkyl, halo$C_{1-4}$alkyl, $C_{1-4}$ alkoxy, halo$C_{1-4}$ alkoxy, $C_{1-4}$ alkanoyl and NR'R"; or $R_6$ is a phenyl group, a 5-14 membered heterocyclic group and any of such phenyl or heterocyclic group is optionally substituted by 1, 2, 3 or 4 substituents selected from the group consisting of: halogen, cyano, halo$C_{1-4}$alkyl, $C_{1-4}$alkoxy, $C_{1-4}$alkanoyl and $SF_5$;
$R_7$ is selected in the group consisting of: hydrogen, halogen, hydroxy, cyano, $C_{1-4}$alkyl, $C_{3-7}$ cycloalkyl, $C_{1-4}$alkoxy, halo$C_{1-4}$alkoxy, $C_{1-4}$alkanoyl and NR'R"; or $R_7$ is a phenyl group, a 5-14 membered heterocyclic group; and any of such phenyl or heterocyclic group is optionally substituted by 1, 2, 3 or 4 substituents selected from the group consisting of: halogen, cyano, $C_{1-4}$alkyl, halo$C_{1-4}$alkyl, $C_{1-4}$alkoxy, $C_{1-4}$alkanoyl and $SF_5$;
$R_8$ is selected in the group consisting of: hydrogen, halogen, hydroxy, cyano, $C_{3-7}$ cycloalkyl, halo$C_{1-4}$alkyl, $C_{1-4}$alkoxy, halo$C_{1-4}$alkoxy, $C_{1-4}$alkanoyl and NR'R"; or $R_8$ is a phenyl group, a 5-14 membered heterocyclic group; and any of such phenyl or heterocyclic group is optionally substituted by 1, 2, 3 or 4 substituents selected from the group consisting of: halogen, cyano, haloC$_{1-4}$alkyl, C$_{1-4}$alkoxy, C$_{1-4}$alkanoyl and SF$_5$;

R$_9$ is selected in the group consisting of hydrogen, a phenyl group, a heterocyclyl group, a 5- or 6-membered monocyclic heteroaryl group, and a 8- to 11-membered heteroaryl bicyclic, any of which groups is optionally substituted by 1, 2, 3 or 4 substituents selected from the group consisting of: halogen, cyano, C$_{1-4}$ alkyl, haloC$_{1-4}$ alkyl, C$_{1-4}$alkoxy and C$_{1-4}$alkanoyl;

R$_{10}$ is C$_{1-4}$alkyl;

R$_{11}$ is hydrogen or C$_{1-4}$alkyl;

R' is H, C$_{1-4}$ alkyl or C$_{1-4}$alkanoyl;

R" is defined as R';

R' and R" taken together with the interconnecting nitrogen atom may form a 5-, 6-membered saturated or unsaturated heterocyclic ring;

wherein R$_5$, R$_6$, R$_7$ and R$_8$ are not simultaneously other than hydrogen; wherein only one R$_2$ group ma be different from hydrogen and wherein when n is 0, X is a group —CR$_1$R$_3$—.

The term 'C$_{1-4}$ alkyl' as used herein as a group or a part of the group refers to a linear or branched alkyl group containing from 1 to 4 carbon atoms; examples of such groups include methyl, ethyl, propyl, isopropyl, n-butyl, isobutyl, tert butyl.

The term 'C$_{3-7}$ cycloalkyl group' as used herein means a non aromatic monocyclic hydrocarbon ring of 3 to 7 carbon atom such as, for example, cyclopropyl, cyclobutyl, cyclopentyl, cyclohexyl or cycloheptyl; while unsaturated cycloalkyls include cyclopentenyl and cyclohexenyl, and the like.

The term 'C$_{1-4}$ alkoxy group' as used herein may be a linear or a branched chain alkoxy group, for example methoxy, ethoxy, propoxy, prop-2-oxy, butoxy, but-2-oxy or methylprop-2-oxy and the like.

The term 'C$_{1-4}$ alkanoyl group' as used herein may be a linear or a branched chain alkanoyl group, for example acetyl, ethylcarbonyl, n-propylcarbonyl, i-propyl carbonyl, n-butylcarbonyl or t-butylcarbonyl and the like.

The term 'halogen' as used herein refers to a fluorine, chlorine, bromine or iodine atom.

The term 'halo C$_{1-4}$ alkyl' as used herein means an alkyl group having one or more carbon atoms and wherein at least one hydrogen atom is replaced with halogen such as for example a trifluoromethyl group and the like.

The term 'halo C$_{1-4}$ alkoxy group' as used herein may be a C$_{1-4}$ alkoxy group as defined before substituted with at least one halogen, preferably fluorine, such as OCHF$_2$, or OCF$_3$.

The term 'aryl' as used herein means an aromatic carbocyclic moiety such as phenyl, biphenyl or naphthyl.

The term '5,6-membered monocyclic heteroaryl' as used herein means an aromatic monocyclic heterocycle ring of 5 or 6 members and having at least one heteroatom selected from nitrogen, oxygen and sulfur, and containing at least 1 carbon atom.

Representative 5, 6 membered monocyclic heteroaryl groups include (but are not limited to): furyl, thiophenyl, pyrrolyl, pyridyl, oxazolyl, isooxazolyl, pyrazolyl, imidazolyl, thiazolyl, isothiazolyl, pyridazinyl, pyrimidinyl, pyrazinyl, triazinyl, triazolyl and tetrazolyl.

The term '8,11-membered bicyclic heteroaryl' as used herein means an aromatic bicyclic heterocycle ring of 8 to 11 members and having at least one heteroatom selected from nitrogen, oxygen and sulfur, and containing at least 1 carbon atom.

Representative 8, to 11 membered bicyclic heteroaryl groups include (but are not limited to): benzofuranyl, benzothiophenyl, indolyl, isoindolyl, azaindolyl, quinolinyl, isoquinolinyl, benzoxazolyl, benzimidazolyl, benzothiazolyl, quinazolinyl and phthalazinyl.

The term 5-14 membered heterocycle means a 5 to 7-membered monocyclic, or 7- to 14-membered polycyclic, heterocycle ring which is either saturated, unsaturated or aromatic, and which contains from 1 to 4 heteroatoms independently selected from nitrogen, oxygen and sulfur, and wherein the nitrogen and sulfur heteroatoms may be optionally oxidized, and the nitrogen heteroatom may be optionally quaternized, including bicyclic rings in which any of the above heterocycles are fused to a benzene ring as well as tricyclic (and higher) heterocyclic rings. The heterocycle may be attached via any heteroatom or carbon atom. Heterocycles include heteroaryls as defined above. Thus, in addition to the aromatic heteroaryls listed above, heterocycles also include (but are not limited to) morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydropyrimidinyl, tetrahydrothiophenyl, tetrahydrothiopyranyl, tetrahydropyrimidinyl, tetrahydrothiophenyl, tetrahydrothiopyranyl, and the like.

Any of these groups may be attached to the rest of the molecule at any suitable position.

As used herein, the term "salt" refers to any salt of a compound according to the present invention prepared from an inorganic or organic acid or base, quaternary ammonium salts and internally formed salts. Pharmaceutically acceptable salts are particularly suitable for medical applications because of their greater aqueous solubility relative to the parent compounds. Such salts must clearly have a physiologically acceptable anion or cation. Suitably pharmaceutically acceptable salts of the compounds of the present invention include acid addition salts formed with inorganic acids such as hydrochloric, hydrobromic, hydroiodic, phosphoric, metaphosphoric, nitric and sulfuric acids, and with organic acids, such as tartaric, acetic, trifluoroacetic, citric, malic, lactic, fumaric, benzoic, formic, propionic, glycolic, gluconic, maleic, succinic, camphorsulfuric, isothionic, mucic, gentisic, isonicotinic, saccharic, glucuronic, furoic, glutamic, ascorbic, anthranilic, salicylic, phenylacetic, mandelic, embonic (pamoic), methanesulfonic, ethanesulfonic, pantothenic, stearic, sulfinilic, alginic, galacturonic and arylsulfonic, for example benzenesulfonic and p-toluenesulfonic, acids; base addition salts formed with alkali metals and alkaline earth metals and organic bases such as N,N-dibenzylethylenediamine, chloroprocaine, choline, diethanolamine, ethylenediamine, meglumaine (N-methylglucamine), lysine and procaine; and internally formed salts. Salts having a non-pharmaceutically acceptable anion or cation are within the scope of the invention as useful intermediates for the preparation of pharmaceutically acceptable salts and/or for use in non-therapeutic, for example, in vitro, situations.

Certain of the compounds of the invention may form acid addition salts with one or more equivalents of the acid. The present invention includes within its scope all possible stoichiometric and non-stoichiometric forms.

Pharmaceutically acceptable salts may also be prepared from other salts, including other pharmaceutically acceptable salts, of the compound of formula (I) using conventional methods.

Those skilled in the art of organic chemistry will appreciate that many organic compounds can form complexes with solvents in which they are reacted or from which they are precipitated or crystallized. These complexes are known as "solvates". For example, a complex with water is known as a "hydrate". Solvates of the compound of the invention are within the scope of the invention. The compounds of formula (I) may readily be isolated in association with solvent molecules by crystallisation or evaporation of an appropriate solvent to give the corresponding solvates.

In addition, prodrugs are also included within the context of this invention. As used herein, the term "prodrug" means a compound which is converted within the body, e.g. by hydrolysis in the blood, into its active form that has medical effects. Pharmaceutically acceptable prodrugs are described in T. Higuchi and V. Stella, Prodrugs as Novel Delivery Systems, Vol. 14 of the A.C.S. Symposium Series, Edward B. Roche, ed., Bioreversible Carriers in Drug Design, American Pharmaceutical Association and Pergamon Press, 1987, and in D. Fleisher, S. Ramon and H. Barbra "Improved oral drug delivery: solubility limitations overcome by the use of prodrugs", Advanced Drug Delivery Reviews (1996) 19(2) 115-130, each of which are incorporated herein by reference.

Prodrugs are any covalently bonded carriers that release a compound of structure (I) in vivo when such prodrug is administered to a patient. Prodrugs are generally prepared by modifying functional groups in a way such that the modification is cleaved, either by routine manipulation or in vivo, yielding the parent compound. Prodrugs include, for example, compounds of this invention wherein hydroxy, amine or sulfhydryl groups are bonded to any group that, when administered to a patient, cleaves to form the hydroxy, amine or sulfhydryl groups. Thus, representative examples of prodrugs include (but are not limited to) acetate, formate and benzoate derivatives of alcohol, sulfhydryl and amine functional groups of the compounds of structure (I). Further, in the case of a carboxylic acid (—COOH), esters may be employed, such as methyl esters, ethyl esters, and the like. Esters may be active in their own right and/or be hydrolysable under in vivo conditions in the human body. Suitable pharmaceutically acceptable in vivo hydrolysable ester groups include those which break down readily in the human body to leave the parent acid or its salt.

Furthermore, some of the crystalline forms of the compounds of structure (I) or salts thereof, may exist as polymorphs, which are included in the present invention.

Hereinafter, compounds of formula (I) and their pharmaceutically acceptable salts, solvates and prodrugs defined in any aspect of the invention (except intermediate compounds in chemical processes) are referred to as "compounds of the invention".

Those skilled in the art will appreciate that in the preparation of the compounds of the invention, it may be necessary and/or desirable to protect one or more sensitive groups in the molecule to prevent undesirable side reactions. Suitable protecting groups for use according to the present invention are well known to those skilled in the art and may be used in a conventional manner. See, for example, "Protective groups in organic synthesis" by T. W. Greene and P. G. M. Wuts (John Wiley & sons 1991) or "Protecting Groups" by P. J. Kocienski (Georg Thieme Verlag 1994). Examples of suitable amino protecting groups include acyl type protecting groups (e.g. formyl, trifluoroacetyl, acetyl), aromatic urethane type protecting groups (e.g. benzyloxycarbonyl (Cbz) and substituted Cbz), aliphatic urethane protecting groups (e.g. 9-fluorenylmethoxycarbonyl (Fmoc), t-butyloxycarbonyl (Boc), isopropyloxycarbonyl, cyclohexyloxycarbonyl) and alkyl type protecting groups (e.g. benzyl, trityl, chlorotrityl). Examples of suitable oxygen protecting groups may include for example alky silyl groups, such as trimethylsilyl or tert-butyldimethylsilyl; alkyl ethers such as tetrahydropyranyl or tert-butyl; or esters such as acetate.

The present invention also includes isotopically-labelled compounds, which are identical to those recited in formula (I) and following, but for the fact that one or more atoms are replaced by an atom having an atomic mass or mass number different from the atomic mass or mass number usually found in nature. Examples of isotopes that can be incorporated into compounds of the invention and pharmaceutically acceptable salts thereof include isotopes of hydrogen, carbon, nitrogen, oxygen, phosphorous, sulphur, fluorine, iodine, and chlorine, such as $^{2}H$, $^{3}H$, $^{11}C$, $^{13}C$, $^{14}C$, $^{15}N$, $^{17}O$, $^{18}O$, $^{31}P$, $^{32}P$, $^{35}S$, $^{18}F$, $^{36}Cl$, $^{123}I$ and $^{128}I$.

Compounds of the present invention and non-pharmaceutically acceptable salts thereof that contain the aforementioned isotopes and/or other isotopes of other atoms are within the scope of the present invention. Isotopically-labelled compounds of the present invention, for example those into which radioactive isotopes such as $^{3}H$, $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. $^{11}C$ and $^{18}F$ isotopes are particularly useful in PET (positron emission tomography), and $^{125}I$ isotopes are particularly useful in SPECT (single photon emission computerized tomography), all useful in brain imaging. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labelled compounds of the present invention and non-pharmaceutically acceptable salts thereof can generally be prepared by carrying out the procedures disclosed in the Schemes and/or in the Examples below, by substituting a readily available isotopically labelled reagent for a non-isotopically labelled reagent.

Certain groups/substituents included in the present invention may be present as isomers. The present invention includes within its scope all such isomers, including racemates, enantiomers, and mixtures thereof.

It will be appreciated that compounds of formula (I) possess at least one sterogenic center, at the position indicated in the picture below by a * sign:

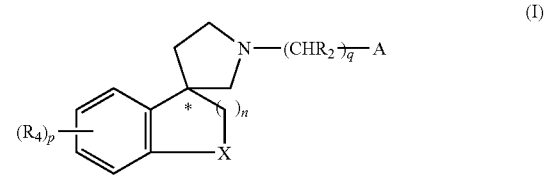

(I)

In one embodiment of the present invention compounds of formula (I)' are provided that correspond to stereochemical isomers of compounds of formula (I), enriched in configuration shown in the picture below at the * stereogenic center

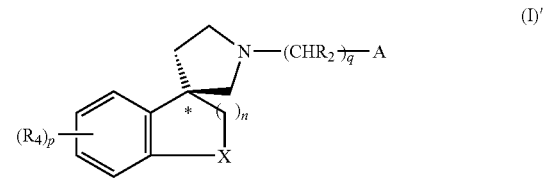

(I)' wherein A, p, q, n, X, $R_4$ and $R_2$ are defined as above for compounds of formula (I), or a salt thereof.

In another embodiment of the present invention compounds of formula (I)'' are provided that correspond to stereochemical isomers of compounds of formula (I), enriched in configuration shown in the picture below at the * stereogenic center

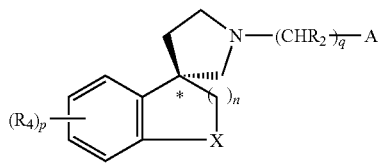

(I)'' wherein A, p, q, n, X, $R_4$ and $R_2$ are defined as above for compounds of formula (I), or a salt thereof.

It is intended in the context of the present invention that stereochemical isomers enriched in the absolute configuration shown in formula (I)' or (I)'' correspond in one embodiment to at least 90% e.e. (enantiomeric excess). In another embodiment the isomers correspond to at least 95% e.e. In another embodiment the isomers correspond to at least 99% e.e.

Certain of the groups included in compounds of formula (I) may exist in one or more tautomeric forms. The present invention includes within its scope all such tautomeric forms, including mixtures.

It will be appreciated by the person skilled in the art that the group (P1a), i.e. a group of formula (P1) wherein $R_{11}$ is hydrogen, in compounds of formula (I) may exist in the tautomeric forms (P1a') and (P1a'') as below described:

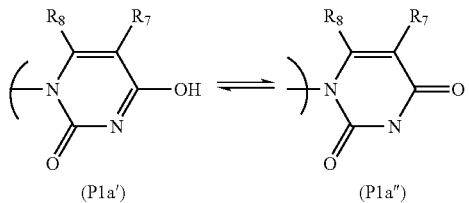

(P1a')    (P1a'')

Both tautomeric forms are intended to be included within the scope of this invention.

In one embodiment, $R_2$ is hydrogen.
In one embodiment q is 3, 4 or 5. In another embodiment q is 3 or 4. In a still further embodiment q is 3.
In one embodiment, p is 0, 1 or 2. In another embodiment, p is 1.
In one embodiment X is —$CR_1R_3$— or —O—. In another embodiment X is —$CR_1R_3$—. In a still further embodiment X is —O—.
In one embodiment $R_1$ is hydrogen, fluorine or methyl. In another embodiment $R_1$ is hydrogen.
In one embodiment $R_3$ is hydrogen, fluorine or methyl. In another embodiment $R_1$ is hydrogen.
In one embodiment, n is 1 or 2. In another embodiment n is 1. In a still further embodiment n is 2.
In one embodiment, $R_4$ is halogen, $C_{1-4}$alkyl or $C_{1-4}$alkoxy. In another embodiment, $R_4$ is hydrogen, bromine, fluorine, chlorine or methoxy.
In one embodiment, A is a group P, P1, P2 or P3. In another embodiment A is a group P1 or P3. In a further embodiment A is a group P1. In a still further embodiment a is a group P3.

In one embodiment, $R_8$ is hydrogen.
In one embodiment, $R_7$ is hydrogen, $C_{1-4}$alkyl or 5, 6 membered monocyclic heteroaryl group. In another embodiment, $R_7$ is hydrogen, methyl or thiophenyl.
In one embodiment, $R_6$ is hydrogen, halogen or $C_{1-4}$alkyl.
In one embodiment, $R_5$ is hydrogen, halogen or $C_{1-4}$alkyl.
In one embodiment, $R_{11}$ is hydrogen.
In one embodiment, $R_{10}$ is methyl.
In one embodiment, $R_9$ is an optionally substituted 5- or 6-membered monocyclic heteroaryl group. In another embodiment, $R_9$ is optionally substituted oxazolyl or optionally substituted thiazolyl.

In one embodiment, a compound of formula (IA) or a salt thereof is provided, wherein $R_1$, $R_2$, $R_3$, $R_4$, p, q, n, $R_7$, $R_{11}$ and $R_8$ are as defined for formula (I):

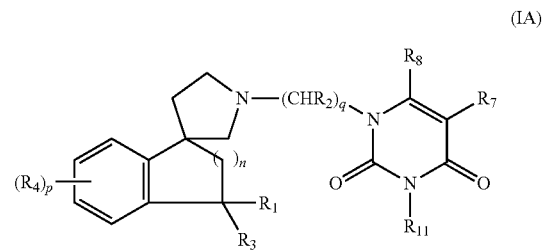

(IA)

In Formula (IA), in one embodiment, q is 3, 4 or 5, $R_2$ is hydrogen, p is 0, 1 or 2, $R_1$ is hydrogen, fluorine or methyl, $R_3$ is hydrogen, fluorine or methyl, n is 1 or 2, $R_4$ is halogen, $C_{1-4}$alkyl or $C_{1-4}$alkoxy, $R_8$ is hydrogen, $R_7$ is hydrogen, $C_{1-4}$alkyl or 5, 6 membered monocyclic heteroaryl group and $R_{11}$ is hydrogen.

In one embodiment, a compound of formula (IB) or a salt thereof is provided, wherein $R_1$, $R_2$, $R_3$, $R_4$, $R_9$, $R_{10}$, p, q, n, $R_7$, $R_{11}$ and $R_8$, are as defined for formula (I):

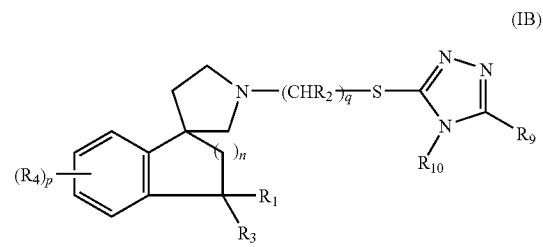

(IB)

In Formula (IB), in one embodiment, q is 3 or 4, $R_2$ is hydrogen, p is 0, 1 or 2, $R_1$ is hydrogen, fluorine or methyl, $R_3$ is hydrogen, fluorine or methyl, n is 1 or 2, $R_4$ is halogen, $C_{1-4}$alkyl or $C_{1-4}$alkoxy, $R_9$ is an optionally substituted 5- or 6-membered monocyclic heteroaryl group and $R_{10}$ is methyl.

Example compounds of the present invention include:
5-bromo-1'-(3-{[3-(4-methyl-1,3-oxazol-5-yl)-1H-1,2,4-triazol-5-yl]thio}propyl)-2,3-dihydrospiro[indene-1,3'-pyrrolidine];
6-bromo-1'-(3-{[4-methyl-5-(4-methyl-1,3-oxazol-5-yl)-4H-1,2,4-triazol-3-yl]thio}propyl)-3,4-dihydro-2H-spiro[naphthalene-1,3'-pyrrolidine]hydrochloride;
1'-(3-{[4-methyl-5-(4-methyl-1,3-oxazol-5-yl)-4H-1,2,4-triazol-3-yl]thio}propyl)-6-(methyloxy)-3,4-dihydro-2H-spiro[naphthalene-1,3'-pyrrolidine]hydrochloride;
4-bromo-1'-(3-{[4-methyl-5-(4-methyl-1,3-oxazol-5-yl)-4H-1,2,4-triazol-3-yl]thio}propyl)-2,3-dihydrospiro[indene-1,3'-pyrrolidine]hydrochloride;

1'-(3-{[4-methyl-5-(4-methyl-1,3-oxazol-5-yl)-4H-1,2,4-triazol-3-yl]thio}propyl)-5-(methyloxy)-3,4-dihydro-2H-spiro[naphthalene-1,3'-pyrrolidine]hydrochloride;

1'-(3-{[4-methyl-5-(4-methyl-1,3-oxazol-5-yl)-4H-1,2,4-triazol-3-yl]thio}propyl)-7-(methyloxy)-3,4-dihydro-2H-spiro[naphthalene-1,3'-pyrrolidine]hydrochloride;

6-bromo-1'-(3-{[4-methyl-5-(4-methyl-1,3-oxazol-5-yl)-4H-1,2,4-triazol-3-yl]thio}propyl)-2,3-dihydrospiro[indene-1,3'-pyrrolidine]hydrochloride;

7-bromo-1'-(3-{[4-methyl-5-(4-methyl-1,3-oxazol-5-yl)-4H-1,2,4-triazol-3-yl]thio}propyl)-3,4-dihydro-2H-spiro[naphthalene-1,3'-pyrrolidine]hydrochloride;

or a salt thereof.

In another embodiment, example compounds of the present invention include:

5-bromo-1'-(3-{[3-(4-methyl-1,3-oxazol-5-yl)-1H-1,2,4-triazol-5-yl]thio}propyl)-2,3-dihydrospiro[indene-1,3'-pyrrolidine];

5-(5-(3-(5-chloro-6-methoxy-2,3-dihydrospiro[indene-1,3'-pyrrolidine]-1'-yl)propylthio)-4-methyl-4H-1,2,4-triazol-3-yl)-2,4-dimethylthiazole;

5-(5-(3-(5-chloro-2,3-dihydrospiro[indene-1,3'-pyrrolidine]-1'-yl)propylthio)-4-methyl-4H-1,2,4-triazol-3-yl)-2,4-dimethylthiazole;

5-(5-(3-(5-chloro-2,3-dihydrospiro[indene-1,3'-pyrrolidine]-1'-yl)propylthio)-4-methyl-4H-1,2,4-triazol-3-yl)-2,4-dimethylthiazole;

5-(5-(3-(5-fluoro-2,3-dihydrospiro[indene-1,3'-pyrrolidine]-1'-yl)propylthio)-4-methyl-4H-1,2,4-triazol-3-yl)-2,4-dimethylthiazole;

5-(5-(3-(5-fluoro-2,3-dihydrospiro[indene-1,3'-pyrrolidine]-1'-yl)propylthio)-4-methyl-4H-1,2,4-triazol-3-yl)-2,4-dimethylthiazole;

1-(4-(5-fluoro-2,3-dihydrospiro[indene-1,3'-pyrrolidine]-1'-yl)butyl)-5-(thiophen-2-yl)pyrimidine-2,4(1H,3H)-dione;

1-(4-(5-chloro-2,3-dihydrospiro[indene-1,3'-pyrrolidine]-1'-yl)butyl)-5-(thiophen-2-yl)pyrimidine-2,4(1H,3H)-dione;

1-(3-(5-fluoro-2,3-dihydrospiro[indene-1,3'-pyrrolidine]-1'-yl)propyl)-5-(thiophen-2-yl)pyrimidine-2,4(1H,3H)-dione hydrochloride;

1-(3-(5-chloro-2,3-dihydrospiro[indene-1,3'-pyrrolidine]-1'-yl)propyl)-5-(thiophen-2-yl)pyrimidine-2,4(1H,3H)-dione 1-[3-(5-bromo-2,3-dihydro-1'H-spiro[indene-1,3'-pyrrolidin]-1'-yl)propyl]-5-methyl-2,4(1H,3H)-pyrimidinedione;

1-[4-(5-bromo-2,3-dihydro-1'H-spiro[indene-1,3'-pyrrolidin]-1'-yl)butyl]-5-methyl-2,4(1H,3H)-pyrimidinedione;

1-[5-(6-bromo-3,4-dihydro-1'-1,2H-spiro[naphthalene-1,3'-pyrrolidin]-1'-yl)pentyl]-5-methyl-2,4(1H,3H)-pyrimidinedione;

6-bromo-1'-(3-{[4-methyl-5-(4-methyl-1,3-oxazol-5-yl)-4H-1,2,4-triazol-3-yl]thio}propyl)-2,3-dihydrospiro[indene-1,3'-pyrrolidine];

4-bromo-1'-(3-{[4-methyl-5-(4-methyl-1,3-oxazol-5-yl)-4H-1,2,4-triazol-3-yl]thio}propyl)-2,3-dihydrospiro[indene-1,3'-pyrrolidine];

6-bromo-1'-(3-{[4-methyl-5-(4-methyl-1,3-oxazol-5-yl)-4H-1,2,4-triazol-3-yl]thio}propyl)-3,4-dihydro-2H-spiro[naphthalene-1,3'-pyrrolidine];

7-bromo-1'-(3-{[4-methyl-5-(4-methyl-1,3-oxazol-5-yl)-4H-1,2,4-triazol-3-yl]thio}propyl)-3,4-dihydro-2H-spiro[naphthalene-1,3'-pyrrolidine];

1'-(3-{[4-methyl-5-(4-methyl-1,3-oxazol-5-yl)-4H-1,2,4-triazol-3-yl]thio}propyl)-7-(methyloxy)-3,4-dihydro-2H-spiro[naphthalene-1,3'-pyrrolidine];

1'-(3-{[4-methyl-5-(4-methyl-1,3-oxazol-5-yl)-4H-1,2,4-triazol-3-yl]thio}propyl)-6-(methyloxy)-3,4-dihydro-2H-spiro[naphthalene-1,3'-pyrrolidine];

1'-(3-{[4-methyl-5-(4-methyl-1,3-oxazol-5-yl)-4H-1,2,4-triazol-3-yl]thio}propyl)-5-(methyloxy)-3,4-dihydro-2H-spiro[naphthalene-1,3'-pyrrolidine];

1,3-oxazol-5-yl)-4H-1,2,4-triazol-3-yl]thio}propyl)-2,3-dihydrospiro[chromene-4,3'-pyrrolidine];

5-(5-(3-(6-fluoro-2,3-dihydrospiro[indene-1,3'-pyrrolidine]-1'-yl)propylthio)-4-methyl-4H-1,2,4-triazol-3-yl)-2,4-dimethylthiazole;

5-(5-(3-(6-chloro-2,3-dihydrospiro[indene-1,3'-pyrrolidine]-1'-yl)propylthio)-4-methyl-4H-1,2,4-triazol-3-yl)-2,4-dimethylthiazole;

or a salt thereof.

Some of the compounds of the present invention may be prepared following some of the procedures described in PCT International Publication WO2005/080382.

The present invention also provides a process for preparing a compound of formula (I) or a salt thereof as defined above, which comprises the steps of:

a) reacting a compound of formula (II):

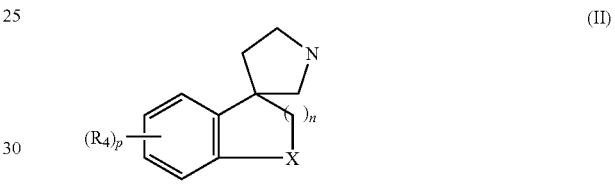

(II)

wherein $R_4$, X, p and n are as defined for formula (I), with a compound of formula (III):

(III)

wherein $R_2$, A and q are as defined for formula (I) and X is a leaving group;

Or b) reacting a compound of formula (II) as above defined with a compound of formula (IV)

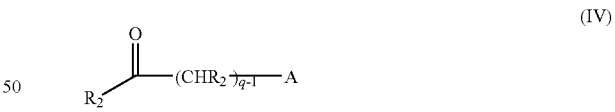

(IV)

wherein $R_2$, A and q are as defined for formula (I);

and thereafter optionally for process (a) or process (b):

(i) removing any protecting group(s); and/or
(ii) forming a salt; and/or
(iii) converting a compound of formula (I) or a salt thereof to another compound of formula
(I)' or a salt thereof.

Process (a) may be performed using conventional methods for the formation of a tertiary amine. The leaving group X can be halogen such as chlorine. Alternatively X can be a sulfonyloxy group such $C_{1-4}$alkylsulfonyloxy (e.g. methanesulfonyloxy), $C_{1-4}$alkylsulfonyloxy or halo$C_{1-4}$alkylsulfonyloxy (e.g. trifluoromethanesulfonyloxy); or arylsulfonyloxy wherein aryl is optionally substituted phenyl, an optionally substituted 5- or 6-membered heteroaromatic group, or an optionally substituted bicyclic group, for example optionally substituted phenyl, wherein in each case the optional substituents are one or more $C_{1-2}$alkyl groups; e.g. para-toluenesulfonyloxy. When X is a halogen the reaction may be carried out using a base such as potassium carbonate in the presence of a source of iodide such as sodium iodide in a solvent such as N,N-dimethylformamide at a suitable temperature, e.g. 60° C.

Process (b) may be performed using conventional methods for the formation of a tertiary amine by means of reductive amination. For example when, for compounds of formula (IV) $R_2$ is hydrogen, the reaction may be carried out using sodium triacetoxy borohydride in a suitable solvent such as 1,2 dichloroethane at 0° C.

Compounds of formula (II) are commercially available or may be prepared according to the following synthetic scheme:

A compound of formula (IIIa), i.e. a compound of formula (III) as above defined, wherein A is a group P, may itself be prepared by reacting a compound of formula (V):

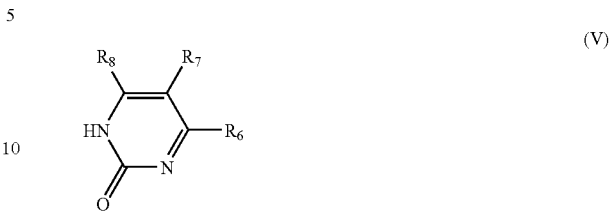

wherein $R_6$, $R_7$ and $R_3$ are as defined as for formula (I), with a compound of formula (VI):

$L(CHR_2)_qX$            (VI)

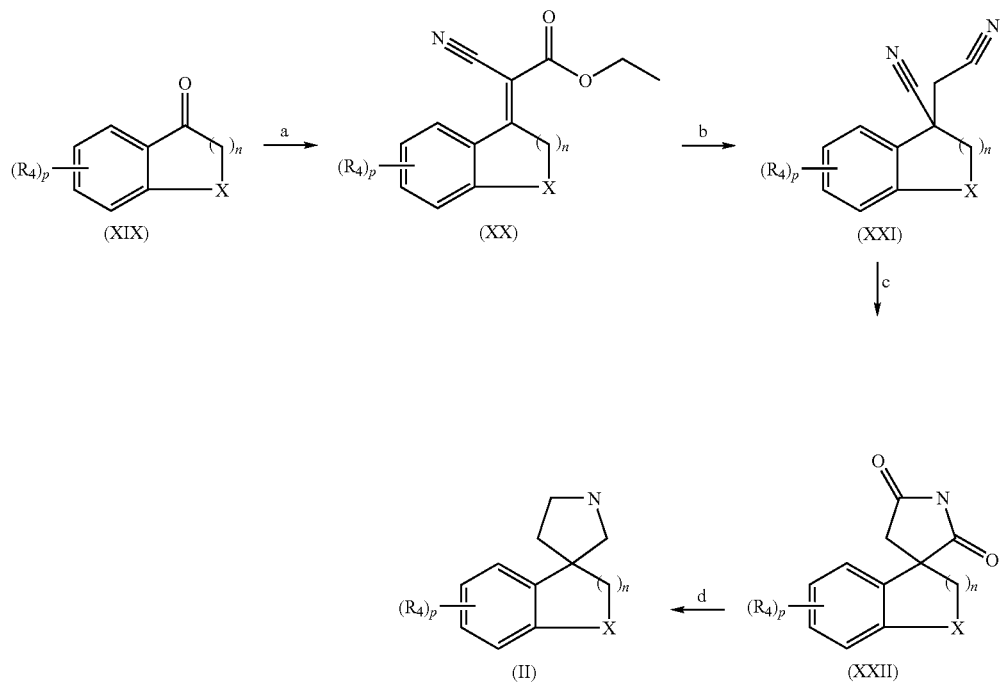

wherein X, $R_4$, p and n are defined as for formula (I) and wherein
- step a means condensation of a compound of formula (XIX) with ethylcyanoacetate with contemporary removal of water to give compounds of formula (XX);
- step b means reaction of compounds of formula (XX) with potassium cyanide in an appropriate solvent (such as ethanol) followed by heating at high temperature (such as 65° C.) to obtain compounds of formula (XXI);
- step c means reaction of compounds of formula (XXI) with glacial acetic acid and sulphuric acid at high temperature (such as 125° C.) to give cyclized compounds of formula (XXII);
- step d means reduction of imide of formula (XXII) with an appropriate reducing agent (such as $BH_3$. THF) in a suitable solvent (such as THF) heating at reflux to give compounds of formula (II).

Compounds of formula (XIX) are commercially available or may be prepared through procedures well known in the literature.

wherein $R_2$ and q are defined as for formula (I), X is as above defined for compounds of formula (III) and L is a leaving group.

The leaving group L can be halogen, such as chlorine. Alternatively L can be a sulfonyloxy group such $C_{1-4}$alkylsulfonyloxy (e.g. methanesulfonyloxy), $C_{1-4}$alkylsulfonyloxy or halo$C_{1-4}$alkylsulfonyloxy (e.g. trifluoromethanesulfonyloxy); or arylsulfonyloxy wherein aryl is optionally substituted phenyl, an optionally substituted 5- or 6-membered heteroaromatic group, or an optionally substituted bicyclic group, for example optionally substituted phenyl, wherein in each case the optional substituents are one or more $C_{1-2}$alkyl groups; e.g. para-toluenesulfonyloxy. When L is a halogen the reaction may be carried out using a base such as potassium carbonate in the presence of a source of iodide such as sodium iodide in a solvent such as N,N-dimethylformamide at a suitable temperature, e.g. 60° C.

A compound of formula (IVa), i.e. a compound of formula (IV) as above defined, wherein A is a group P, may itself be prepared through the following steps:

f) reacting a compound of formula (V):

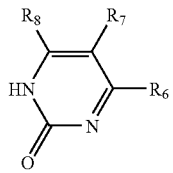

wherein $R_6$, $R_7$ and $R_8$, are as defined as for formula (I), with a compound of formula (VIII)

MCR$_2$(CHR$_2$)$_{q-1}$X (VIII)

wherein $R_2$ and q are defined as for formula (I), X is as above defined for compounds of formula (III) and M is an appropriate carbonylic protecting group (for example dimethylacetale or dioxalane);
and then
g) cleavage of the protecting group.

Cleavage of the protecting group may be carried out under appropriate conditions known to the man skilled in the art. For example, when M is dimethylacetale, the cleavage may carried out by treatment with a diluted solution of hydrochloric acid in dioxane or methanol under gentle heating (e.g. 60° C.).

A compound of formula (IVa), as above defined, may also be prepared through the following steps:
h) reacting a compound of formula (V), as above defined:

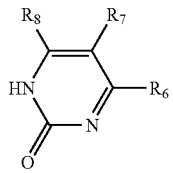

with a compound of formula (IX)

NCR$_2$(CHR$_2$)$_{q-1}$X (IX)

wherein $R_2$ and q are defined as for formula (I), X is as above defined for compounds of formula (III) and N is a protected alcoholic function (for example: terbutyldimethylsilyl);
and then
i) cleavage of the protecting group under appropriate conditions known to the man skilled in the art and subsequent oxidation of the free alcoholic function obtained to carbonyl group.

For example when N is a terbutyl dimethyl silyl protecting group the cleavage can be performed by treatment with a 1N solution of hydrochloric acid in dioxane at 0° C. for 1 hour. Appropriate conditions for the oxidation step comprise Dess-Martin periodinane mediated oxidation in dry THF as solvent at 0° C. for 1 hour.

Compounds of formula (VI), (VIII) and (IX) are commercially available or may be prepared through reactions known in the literature.

Compounds of formula (V) are either commercially available or may be prepared through reactions known in the literature or through the procedures herebelow described.

A suitable synthetic process for the preparation of compounds (Va), wherein $R_7$ and $R_8$ are as defined as for formula (I) and $R_6$ is a phenyl or heteroaryl group, comprises the following steps:

m)

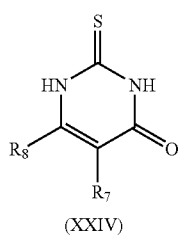 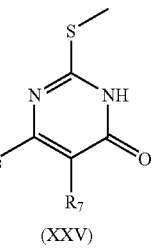

(XXIV) (XXV)

followed by step n):

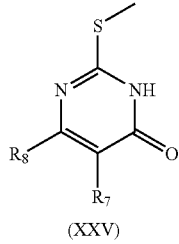 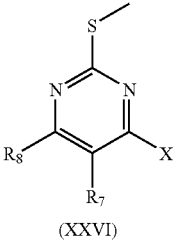

(XXV) (XXVI)

followed by step o):

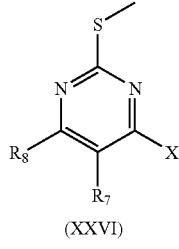 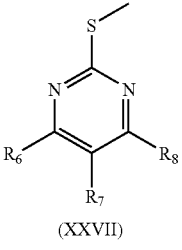

(XXVI) (XXVII)

followed by step p):

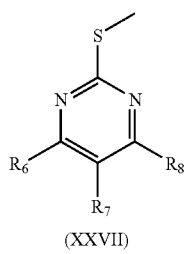 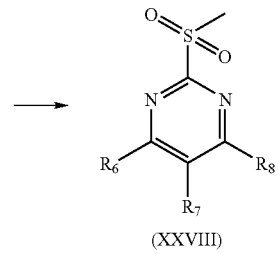

(XXVII) (XXVIII)

and then by step q):

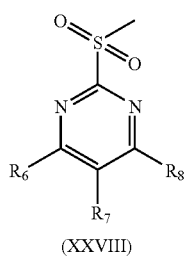 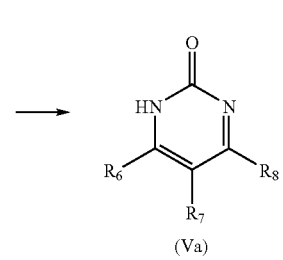

(XXVIII) (Va)

Step m) means sulfur methylation and may be performed starting from compounds of formula (XXIV), wherein $R_7$ and $R_8$ are as defined as for formula (I), using MeI in refluxing ethanol as solvent;

Step n) means conversion of the carbonyl group in compounds of formula (XXV), wherein $R_7$ and $R_8$ are as defined as for formula (I), into a halogen atom and may be performed for example by using POCl3 in dioxane at reflux;

Step (O) means palladium catalyzed coupling of compounds of formula (XXVI), wherein wherein $R_7$ and $R_8$ are as defined as for formula (I) and X is alogen, i.e chlorine or iodine, with the suitable aryl or heteroaryl boronic acids. Step (o) may be performed using convential method for the Suzuky coupling, using for example $Pd(OAc)_2$ as the source of catalytic palladium (0), in the presence of $Na_2CO_3$ as base and a suitable aryl boronic acid or aryl boronic ester in an appropriate solvent, such as nPrOH;

Step p) means oxidation of compounds of formula (XXVII), wherein $R_6$, $R_7$ and $R_8$ are as defined as for formula (I), by means of appropriate oxidative agents such as for example oxone in a suitable solvent i.e. MeOH;

Step q) means basic hydrolysis of the methyl sulphonyl group of compounds of formula (XXVIII), wherein $R_6$, $R_7$ and $R_8$ are as defined as for formula (I), using for example a diluted solution of NaOH at room temperature in dioxane as solvent.

Compounds of formula (XXIV) are either commercially available or may be prepared through reactions known in the literature.

A compound of formula (IIIc), i.e. a compound of formula (III) as above defined wherein A is a group P2, may itself be prepared by reacting a compound of formula (X):

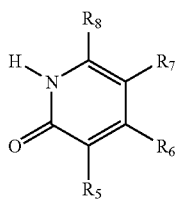

(X)

wherein $R_5$, $R_6$, $R_7$ and $R_8$ are as hereinbefore defined for compounds of formula (I), with a compound of formula (VI) as above defined:

L(CHR$_2$)$q$X    (VI).

A compound of formula (IVc), .e. a compound of formula (IV) as above defined wherein A is a group P2, may itself be prepared through the following steps:

f) reacting a compound of formula (X) as above defined:

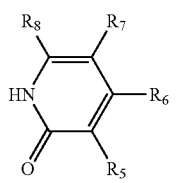

(X)

with a compound of formula (VIII) as above defined

MCR$_2$(CHR$_2$)$_{q-1}$X    (VIII);

and then
g) cleavage of the protecting group. For example procedure, see step g) above.

Compound of formula (IVc), as above defined, may also be prepared through the following steps:
h) reacting a compound of formula (X), as above defined:

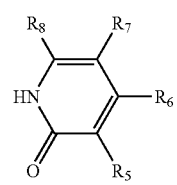

(X)

with a compound of formula (IX) as above defined

NCR$_2$(CHR$_2$)$_{q-1}$X    (IX);

and then
i) cleavage of the protecting group under appropriate conditions known to the man skilled in the art and subsequent oxidation of the free alcoholic function obtained to carbonyl group. For example procedure, see step i) above.

Alternatively compounds of formula (IIIc)', i.e. compounds of formula (IIIc) as above defined wherein $R_3$ is a 5,6-membered heteroaryl, may be prepared through the following steps:

j) reacting a compound of formula (XXIX)

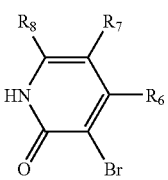

(XXIX)

wherein $R_6$, $R_7$ and $R_6$ are defined as for formula (I), with a compound of formula (VI) as above defined under standard alkylation conditions and then
k) coupling the obtained product of formula (XXX), wherein q, $R_6$, $R_7$ and $R_8$ are defined as for formula (I), $R_5$ is a 5,6 membered heteroaryl group and X is as above defined for compounds of formula (VI),

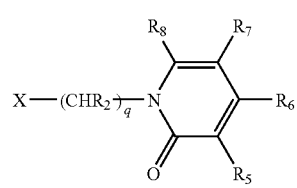

(XXX)

with the appropriate heteroaryl boronic acid or ester.

Step (k) may suitably be performed using convential method for the Suzuky coupling, using for example $Pd(OAc)_2$ as the source of catalytic palladium (0), in the presence of $Na_2CO_3$ as base and a suitable heteroaryl boronic acid or boronic ester in an appropriate solvent, such as nPrOH.

Compounds of formula (X) and (XIX) are commercially available or may be prepared through reactions known in the literature.

A compound of formula (IIId), i.e. a compound of formula (III) as above defined wherein A is a group P3, may itself be prepared by reacting a compound of formula (XXIII):

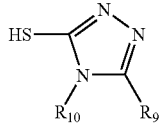

(XXIII)

wherein $R_9$ and $R_{10}$ are as defined for compounds of formula (I), with a compound of formula (VI) as above defined:

L(CHR$_2$)$q$X    (VI).

Reference procedures for the preparation of compound of formula (IIId) may also be found in PCT International Publication WO2005/080382.

Compounds of formula (XIII) are commercially available or may be prepared according to procedures described in PCT International Publication WO2005/080382.

A compound of formula (IIIb), i.e. a compound of formula (III) as above defined wherein A is a group P1, may itself be prepared by reacting a compound of formula (XXXI):

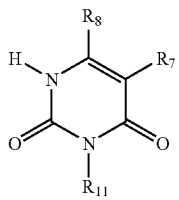

(XXXI)

wherein $R_7$, $R_{11}$ and $R_8$ are as hereinbefore defined for compounds of formula (I), with a compound of formula (VI) as above defined:

L(CHR$_2$)$q$X    (VI).

A compound of formula (IVb), i.e. compounds of formula (IV) as above defined wherein A is a group $P_1$, may be prepared by:

f) reacting a compound of formula (XXXI) as above defined:

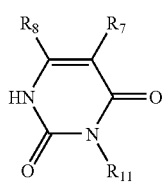

(XXXI)

with a compound of formula (VIII) as above defined:

MCR$_2$(CHR$_2$)$_{q-1}$X    (VIII);

to form a compound of formula (XXXV)

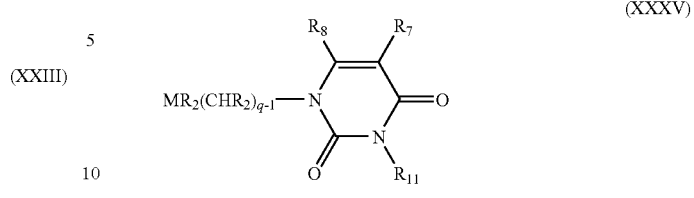

(XXXV)

and then g) cleavage of the protecting group. For example procedure, see step g) above.

A compound of formula (IVb), as above defined, may also be prepared by:

h) reacting a compound of formula (XXXI), as above defined:

(XXXI)

with a compound of formula (IX) as above defined

NCR$_2$(CHR$_2$)$_{q-1}$X    (IX)

to form a compound of formula (XXXII)

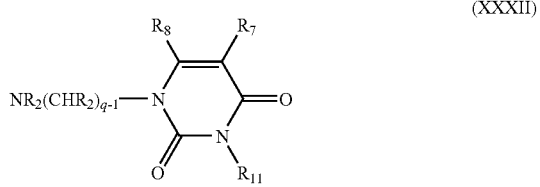

(XXXII)

and then i) cleavage of the protecting group under appropriate conditions known to the man skilled in the art and subsequent oxidation of the free alcoholic function obtained to carbonyl group. For example procedure, see step i) above.

Compounds of formula (XXXI) are either commercially available or may be prepared through reactions known in the literature or through the procedures herebelow described.

Compounds (XXXIa), i.e. compounds of formula (XXXI) wherein $R_8$ is H, $R_{11}$ is H and $R_7$ is a phenyl or a 5,6 membered monocyclic heteroaryl group, may be prepared according to the following synthetic scheme:

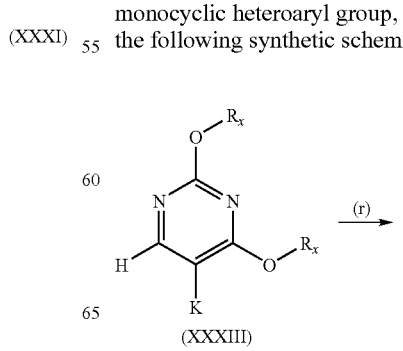

(XXXIII)

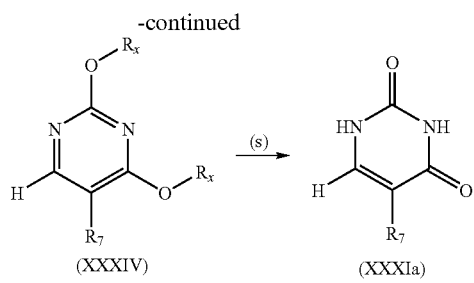

(XXXIV)     (XXXIa)

Step (r) means coupling of compounds of formula (XXXIII) (commercially available, wherein $R_x$ may be a methyl, benzyl or t-butyl group) with a phenyl or heteroaryl boronic acid or ester to give compounds of formula (XXXIV) when K is alogen, i.e. bromine or iodine. When K is boronic acid, step (r) means coupling with a phenyl or heteroaryl alogen derivatives, i.e. bromo or iodo derivatives.

Step (s) means cleavage of the di $R_x$ protecting group to give compound (XXXIa). Suitable conditions for cleavage of methyl or t-butyl protecting groups are acidic conditions; suitable conditions for removal of benzyl comprise the use of $Me_3SiI$ in dichloromethane.

Step (r) may suitably be performed using convential method for the Suzuky coupling, using for example $Pd(OAc)_2$ as the source of catalytic palladium (0), in the presence of $Na_2CO_3$ as base and a suitable aryl boronic acid or aryl boronic ester in an appropriate solvent, such as nPrOH.

Step (s) may be performed typically by using a 4N solution of hydrochloric acid in dioxane as solvent at 0° C. for 1 hour.

A compound of formula (IVd), i.e. compounds of formula (IVb) as above defined wherein A is a group $P_1$ and $R_{11}$ is $C_{1-4}$ alkyl, may be also prepared by reacting a compound of formula (XXXVa), i.e. a compound of formula (XXV) as above defined wherein $R_{11}$ is hydrogen, with the appropriate alkyl iodide of formula $R_{11}I$ under standard alkylation condition. For example the reaction may be performed in DMF and in the presence of $K_2CO_3$ Alkylation step has to be followed by cleavage of the protecting group. For example procedure, see step g) above.

Interconversion reactions between compounds of formula (I) and salts thereof may be performed using methods well known in the art. Examples include:
(i) converting one or more of $R_4$ from alkoxy (e.g. methoxy) to hydroxy,
(ii) converting one or more of $R_4$ from hydroxy to sulfonyloxy, such as alkylsulfonyloxy or haloalkylsulfonyloxy, e.g. methanesulfonyloxy or alkylsulfonyloxy or trifluoro-methanesulfonyloxy,
(iii) converting one or more of $R_4$ from halogen or perfluoroalkylsulfonyloxy to cyano; and optionally thereafter forming a salt of formula (I).

When a specific enantiomer or diastereoisomer of a compound of formula (I) or salts thereof, is required, this may be obtained for example by resolution of a corresponding enantiomeric or diastereosiomeric mixture using conventional methods.

Thus, for example, specific enantiomers or diastereoisomers of the compounds may be obtained from the corresponding enantiomeric or diastereoisomeric mixture using chiral chromatographic methods such as for example chiral HPLC or SFC.

Alternatively a specific enantiomer or diastereoisomer of a compound of general formula (I), or salts thereof, may be synthesised from the appropriate optically active intermediates using any of the general processes described herein.

Compounds of formula (I) or pharmaceutically acceptable salts thereof, have been found to exhibit affinity for dopamine receptors, in particular the $D_3$ receptor, and are expected to be useful in the treatment of disease states which require modulation of such receptors, such as psychotic conditions.

Many of the compounds of formula (I) or pharmaceutically acceptable salts thereof have also been found to have greater affinity for dopamine $D_3$ than for $D_2$ receptors. The therapeutic effect of currently available antipsychotic agents (neuroleptics) is generally believed to be exerted via blockade of $D_2$ receptors; however this mechanism is also thought to be responsible for undesirable extrapyramidal side effects (eps) associated with many neuroleptic agents. It has been suggested that blockade of the recently characterised dopamine $D_3$ receptor may give rise to beneficial antipsychotic activity without significant eps. (see for example Sokoloff et al, Nature, 1990; 347: 146-151; and Schwartz et al, Clinical Neuropharmacology, Vol 16, No. 4, 295-314, 1993). In one embodiment compounds of formula (I) or salts thereof are provided which have higher (e.g. $\geq 10\times$ or $\geq 100\times$ higher) affinity for dopamine $D_3$ than dopamine $D_2$ receptors (such affinity can be measured using standard methodology—see herein).

Compounds of the invention may suitably be used as selective modulators of $D_3$ receptors.

From the localisation of $D_3$ receptors, it could also be envisaged that the compounds could also have utility for the treatment of substance abuse where it has been suggested that $D_3$ receptors are involved (e.g. see Levant, 1997, Pharmacol. Rev., 49, 231-252). Examples of such substance abuse include alcohol, cocaine, heroin and nicotine abuse. Other conditions which may be treated by the compounds include substance related disorders, dyskinetic disorders such as Parkinson's disease, neuroleptic-induced parkinsonism and tardive dyskinesias; depression; anxiety, cognitive impairment including memory disorders such as Alzheimers disease, sexual dysfunction, sleep disorders, emesis, amnesia, aggression, vertigo, dementia, circadian rhythm disorders and gastric motility disorders e.g. IBS.

A wide range of psychiatric and neuropsychiatric disorders appear to be related to Obsessive-Compulsive Disorder, and form a family of related disorders referred to as obsessive-compulsive (OC) spectrum disorders. The compounds of the invention may be used for the treatment of an obsessive-compulsive spectrum disorder, including somatoform disorders such as body dysmorphic disorder and hyperchondriasis, bulimia nervosa, anorexia nervosa, binge eating, paraphilia and nonparaphilic sexual addictions, Sydeham's chorea, torticollis, autism, compulsive hoarding, and movement disorders, including Tourette's syndrome. As used herein, the phrase "obsessive-compulsive spectrum disorder" is intended to include Obsessive-Compulsive Disorder.

The compounds of the invention are also useful for the treatment of premature ejaculation.

The terms describing the indications used herein are classified in the Diagnostic and Statistical Manual of Mental Disorders, 4th Edition, published by the American Psychiatric Association (DSM-IV) and/or the International Classification of Diseases, 10th Edition (ICD-10). The various subtypes of the disorders mentioned herein are contemplated as part of the present invention. Numbers in brackets after the listed diseases below refer to the classification code in DSM-IV.

The term "psychotic disorder" includes:
Schizophrenia including the subtypes Paranoid Type (295.30), Disorganised Type (295.10), Catatonic Type (295.20), Undifferentiated Type (295.90) and Residual Type (295.60); Schizophreniform Disorder (295.40); Schizoaffective Disorder (295.70) including the subtypes Bipolar Type and Depressive Type; Delusional Disorder (297.1) including the subtypes Erotomanic Type, Grandiose Type, Jealous Type, Persecutory Type, Somatic Type, Mixed Type and Unspecified Type; Brief Psychotic Disorder (298.8); Shared Psychotic Disorder (297.3); Psychotic Disorder Due to a General Medical Condition including the subtypes With Delusions and With Hallucinations; Substance-Induced Psychotic Disorder including the subtypes With Delusions (293.81) and With Hallucinations (293.82); and Psychotic Disorder Not Otherwise Specified (298.9).

The term "substance-related disorder" includes:

Substance-related disorders including Substance Use Disorders such as Substance Dependence, Substance Craving and Substance Abuse; Substance-Induced Disorders such as Substance Intoxication, Substance Withdrawal, Substance-Induced Delirium, Substance-Induced Persisting Dementia, Substance-Induced Persisting Amnestic Disorder, Substance-Induced Psychotic Disorder, Substance-Induced Mood Disorder, Substance-Induced Anxiety Disorder, Substance-Induced Sexual Dysfunction, Substance-Induced Sleep Disorder and Hallucinogen Persisting Perception Disorder (Flashbacks); Alcohol-Related Disorders such as Alcohol Dependence (303.90), Alcohol Abuse (305.00), Alcohol Intoxication (303.00), Alcohol Withdrawal (291.81), Alcohol Intoxication Delirium, Alcohol Withdrawal Delirium, Alcohol-Induced Persisting Dementia, Alcohol-Induced Persisting Amnestic Disorder, Alcohol-Induced Psychotic Disorder, Alcohol-Induced Mood Disorder, Alcohol-Induced Anxiety Disorder, Alcohol-Induced Sexual Dysfunction, Alcohol-Induced Sleep Disorder and Alcohol-Related Disorder Not Otherwise Specified (291.9); Amphetamine (or Amphetamine-Like)-Related Disorders such as Amphetamine Dependence (304.40), Amphetamine Abuse (305.70), Amphetamine Intoxication (292.89), Amphetamine Withdrawal (292.0), Amphetamine Intoxication Delirium, Amphetamine Induced Psychotic Disorder, Amphetamine-Induced Mood Disorder, Amphetamine-Induced Anxiety Disorder, Amphetamine-Induced Sexual Dysfunction, Amphetamine-Induced Sleep Disorder and Amphetamine-Related Disorder Not Otherwise Specified (292.9); Caffeine Related Disorders such as Caffeine Intoxication (305.90), Caffeine-Induced Anxiety Disorder, Caffeine-Induced Sleep Disorder and Caffeine-Related Disorder Not Otherwise Specified (292.9); Cannabis-Related Disorders such as Cannabis Dependence (304.30), Cannabis Abuse (305.20), Cannabis Intoxication (292.89), Cannabis Intoxication Delirium, Cannabis-Induced Psychotic Disorder, Cannabis-Induced Anxiety Disorder and Cannabis-Related Disorder Not Otherwise Specified (292.9); Cocaine-Related Disorders such as Cocaine Dependence (304.20), Cocaine Abuse (305.60), Cocaine Intoxication (292.89), Cocaine Withdrawal (292.0), Cocaine Intoxication Delirium, Cocaine-Induced Psychotic Disorder, Cocaine-Induced Mood Disorder, Cocaine-Induced Anxiety Disorder, Cocaine-Induced Sexual Dysfunction, Cocaine-Induced Sleep Disorder and Cocaine-Related Disorder Not Otherwise Specified (292.9); Hallucinogen-Related Disorders such as Hallucinogen Dependence (304.50), Hallucinogen Abuse (305.30), Hallucinogen Intoxication (292.89), Hallucinogen Persisting Perception Disorder (Flashbacks) (292.89), Hallucinogen Intoxication Delirium, Hallucinogen-Induced Psychotic Disorder, Hallucinogen-Induced Mood Disorder, Hallucinogen-Induced Anxiety Disorder and Hallucinogen-Related Disorder Not Otherwise Specified (292.9); Inhalant-Related Disorders such as Inhalant Dependence (304.60), Inhalant Abuse (305.90), Inhalant Intoxication (292.89), Inhalant Intoxication Delirium, Inhalant-Induced Persisting Dementia, Inhalant-Induced Psychotic Disorder, Inhalant-Induced Mood Disorder, Inhalant-Induced Anxiety Disorder and Inhalant-Related Disorder Not Otherwise Specified (292.9); Nicotine-Related Disorders such as Nicotine Dependence (305.1), Nicotine Withdrawal (292.0) and Nicotine-Related Disorder Not Otherwise Specified (292.9); Opioid-Related Disorders such as Opioid Dependence (304.00), Opioid Abuse (305.50), Opioid Intoxication (292.89), Opioid Withdrawal (292.0), Opioid Intoxication Delirium, Opioid-Induced Psychotic Disorder, Opioid-Induced Mood Disorder, Opioid-Induced Sexual Dysfunction, Opioid-Induced Sleep Disorder and Opioid-Related Disorder Not Otherwise Specified (292.9); Phencyclidine (or Phencyclidine-Like)-Related Disorders such as Phencyclidine Dependence (304.60), Phencyclidine Abuse (305.90), Phencyclidine Intoxication (292.89), Phencyclidine Intoxication Delirium, Phencyclidine-Induced Psychotic Disorder, Phencyclidine-Induced Mood Disorder, Phencyclidine-Induced Anxiety Disorder and Phencyclidine-Related Disorder Not Otherwise Specified (292.9); Sedative-, Hypnotic-, or Anxiolytic-Related Disorders such as Sedative, Hypnotic, or Anxiolytic Dependence (304.10), Sedative, Hypnotic, or Anxiolytic Abuse (305.40), Sedative, Hypnotic, or Anxiolytic Intoxication (292.89), Sedative, Hypnotic, or Anxiolytic Withdrawal (292.0), Sedative, Hypnotic, or Anxiolytic Intoxication Delirium, Sedative, Hypnotic, or Anxiolytic Withdrawal Delirium, Sedative-, Hypnotic-, or Anxiolytic-Persisting Dementia, Sedative-, Hypnotic-, or Anxiolytic-Persisting Amnestic Disorder, Sedative-, Hypnotic-, or Anxiolytic-Induced Psychotic Disorder, Sedative-, Hypnotic-, or Anxiolytic-Induced Mood Disorder, Sedative-, Hypnotic-, or Anxiolytic-Induced Anxiety Disorder Sedative-, Hypnotic-, or Anxiolytic-Induced Sexual Dysfunction, Sedative-, Hypnotic-, or Anxiolytic-Induced Sleep Disorder and Sedative-, Hypnotic-, or Anxiolytic-Related Disorder Not Otherwise Specified (292.9); Polysubstance-Related Disorder such as Polysubstance Dependence (304.80); and Other (or Unknown) Substance-Related Disorders such as Anabolic Steroids, Nitrate Inhalants and Nitrous Oxide.

Compounds of the invention may be useful for the treatment of cognition impairment.

The term "cognition impairment" includes cognition impairment in other diseases such as schizophrenia, bipolar disorder, depression, other psychiatric disorders and psychotic conditions associated with cognitive impairment, e.g. Alzheimer's disease.

In a further aspect therefore the present invention provides a method of treating a condition for which modulation of dopamine receptors (especially dopamine $D_3$ receptors) is beneficial, which comprises administering to a mammal (e.g. human) in need thereof an effective amount of a compound of the invention.

Modulation, as used herein, especially refers to inhibition/antagonism (which may also translate into inverse agonism in constitutively active receptor systems).

In one embodiment, the condition is a substance-related disorder, a psychotic disorder, an obsessive compulsive spectrum disorder or premature ejaculation.

The invention also provides a compound of the invention for use in therapy.

The invention also provides a compound of the invention for use in the treatment of a condition in a mammal for which modulation of dopamine receptors (especially dopamine $D_3$ receptors) is beneficial.

The invention also provides the use of a compound of the invention in the manufacture of a medicament for the treatment of a condition in a mammal for which modulation of dopamine receptors (especially dopamine $D_3$ receptors) is beneficial.

In one embodiment, compounds of the invention are used in the treatment of psychoses such as schizophrenia, in the treatment of substance abuse, in the treatment of obsessive compulsive spectrum disorders, in the treatment of premature ejaculation.

Also provided is the use of a compound of the invention in the manufacture of a medicament for the treatment of a psychotic condition, substance abuse in a mammal, obsessive compulsive spectrum disorders, and premature ejaculation.

Also provided is a compound of the invention for use in the treatment of a psychotic condition (e.g. schizophrenia), substance abuse, obsessive compulsive spectrum disorders, and premature ejaculation in a mammal.

Also provided is a compound of the invention or for use as an active therapeutic substance in a mammal, e.g. for use in the treatment of any of the conditions described herein.

"Treatment" includes prophylaxis, where this is appropriate for the relevant condition(s).

For use in medicine, the compounds of the present invention are usually administered as a standard pharmaceutical composition. The present invention therefore provides in a further aspect a pharmaceutical composition comprising a compound of the invention and a pharmaceutically acceptable carrier. The pharmaceutical composition can be for use in the treatment of any of the conditions described herein.

Compound of the invention may be administered by any convenient method, for example by oral, parenteral (e.g. intravenous), buccal, sublingual, nasal, rectal or transdermal administration and the pharmaceutical compositions adapted accordingly.

Compound of the invention which are active when given orally can be formulated as liquids or solids, for example syrups, suspensions or emulsions, tablets, capsules and lozenges.

A liquid formulation will generally consist of a suspension or solution of the compound or pharmaceutically acceptable salt in a suitable liquid carrier(s) for example an aqueous solvent such as water, ethanol or glycerine, or a non-aqueous solvent, such as polyethylene glycol or an oil. The formulation may also contain a suspending agent, preservative, flavouring or colouring agent.

A composition in the form of a tablet can be prepared using any suitable pharmaceutical carrier(s) routinely used for preparing solid formulations. Examples of such carriers include magnesium stearate, starch, lactose, sucrose and cellulose.

A composition in the form of a capsule can be prepared using routine encapsulation procedures. For example, pellets containing the active ingredient can be prepared using standard carriers and then filled into a hard gelatin capsule; alternatively, a dispersion or suspension can be prepared using any suitable pharmaceutical carrier(s), for example aqueous gums, celluloses, silicates or oils and the dispersion or suspension then filled into a soft gelatin capsule.

Typical parenteral compositions consist of a solution or suspension of the compound or pharmaceutically acceptable salt in a sterile aqueous carrier or parenterally acceptable oil, for example polyethylene glycol, polyvinyl pyrrolidone, lecithin, arachis oil or sesame oil. Alternatively, the solution can be lyophilised and then reconstituted with a suitable solvent just prior to administration.

Compositions for nasal administration may conveniently be formulated as aerosols, drops, gels and powders. Aerosol formulations typically comprise a solution or fine suspension of the active substance in a pharmaceutically acceptable aqueous or non-aqueous solvent and are usually presented in single or multidose quantities in sterile form in a sealed container, which can take the form of a cartridge or refill for use with an atomising device. Alternatively the sealed container may be a unitary dispensing device such as a single dose nasal inhaler or an aerosol dispenser fitted with a metering valve which is intended for disposal once the contents of the container have been exhausted. Where the dosage form comprises an aerosol dispenser, it will contain a propellant which can be a compressed gas such as compressed air or an organic propellant such as a fluoro-chlorohydrocarbon. The aerosol dosage forms can also take the form of a pump-atomiser.

Compositions suitable for buccal or sublingual administration include tablets, lozenges and pastilles, wherein the active ingredient is formulated with a carrier such as sugar and acacia, tragacanth, or gelatin and glycerin.

Compositions for rectal administration are conveniently in the form of suppositories containing a conventional suppository base such as cocoa butter.

Compositions suitable for transdermal administration include ointments, gels and patches.

In one embodiment, the composition is in unit dose form such as a tablet, capsule or ampoule.

Each dosage unit for oral administration contains for example from 1 to 250 mg (and for parenteral administration contains for example from 0.1 to 25 mg) of a compound of the invention calculated as the free base.

The compounds of the invention will normally be administered in a daily dosage regimen (for an adult patient) of, for example, an oral dose of between 1 mg and 500 mg, for example between 10 mg and 400 mg, e.g. between 10 and 250 mg or an intravenous, subcutaneous, or intramuscular dose of between 0.1 mg and 100 mg, for example between 0.1 mg and 50 mg, e.g. between 1 and 25 mg of the compound of the formula (I) or a pharmaceutically acceptable salt thereof calculated as the free base, the compound being administered 1 to 4 times per day. Suitably the compounds will be administered for a period of continuous therapy, for example for a week or more.

Biological Test Methods

Functional potency of compounds of this invention can be measured by the following GTPS scintillation proximity assay (GTPS-SPA). Cells used in the study are Chinese Hamster Ovary (CHO) Cells.

Cell Line
CHO_D2
CHO_D3

Dopamine CHO $D_3$ (Biocat no 1060) transduced with bacmam G0 G-protein (Biocat no 97886)

All steps are performed at 4° C. Cell membranes are prepared as follows. Cell pellets are resuspended in 10 volumes of 50 mM HEPES, 1 mM EDTA pH 7.4, using KOH.

Cells are homogenised within a glass waring blender for 2 bursts of 15 secs in 200 mls of buffer (50 mM HEPES, 1 mM leupeptin, 25 µg/ml bacitracin, 1 mM EDTA, 1 mM PMSF, 2 µM Pepstatin A). (the latter 2 reagents added as fresh ×100 and ×500 stocks respectively in ethanol). The blender is plunged into ice for 5 mins after the first burst and 10-40 mins after the final burst to allow foam to dissipate. The material is then spun at 500 g for 20 mins and the supernatant spun for 36 mins at 48,000 g. The pellet is resuspended in the same buffer as above but without PMSF and Pepstatin A. The material is then forced through a 0.6 mm needle, made up to the required volume, (usually ×4 the volume of the original cell pellet), aliquoted and stored frozen at −80° C.

The final top concentration of test drug is 3 µM in the assay and 11 points serial dilution curves 1:4 in 100% DMSO are carried out using a Biomek FX. The test drug at 1% (0.5 ul) total assay volume (TAV) is added to a solid, white Greiner polypropylene 384-well assay plate. 50% TAV (25 µl) of precoupled (for 60 mins at RT) membranes, 5 µg/well, and Wheatgerm Agglutinin Polystyrene Scintillation Proximity Assay beads (RPNQ0260, Amersham), 0.25 mg/well, in 20 mM HEPES (pH 7.4, 100 mM NaCl, 10 mM MgCl2), 60 µg/mL saponin and 30 uM GDP is added. The third addition is a 20% TAV (10 ul) addition of either buffer, (agonist format) or EC80 final assay concentration of agonist, Quinelorane, prepared in assay buffer (antagonist format). The assay is started by the addition of 29% TAV (15 ul) of GTP[35S] 0.38 nM final (37NIBq/mL, 1160 Ci/mmol, Amersham). After all additions assay plates are spun down for 1 min at 1,000 rpm. The final assay cocktail (45.5 µl) is incubated at room temperature to equilibrate for 3-6 hours before reading on a ViewLux™ (613/55 filter) luminescence imager 5 min/plate.

The effect of the test drug over the basal generates fpKi values of test drug are calculated from the $IC_{50}$ generated by "antagonist format" experiment, using Cheng & Prusoff equation: fKi=IC50/1+([A]/EC50) where: [A] is the concentration of the agonist Quinelorane in the assay and EC50 is the Quinelorane EC50 value obtained in the same experiment. fpKi is defined as –log fKi.

pKi results are only estimated to be accurate to about 0.3-0.5.

In the context of the present invention functional pKi (fpKi, corresponding to the negative logarithm of fKi) is used instead of functional Ki (fKi) and the compounds of formula (I) and salts thereof typically show fpKi for D3 receptors comprised between approximately 6.5 and 9.0.

EXAMPLES

The invention is further illustrated by the following non-limiting examples.

In the procedures that follow, after each starting material, reference to a Preparation or Example by number is typically provided. This is provided merely for assistance to the skilled chemist. The starting material may not necessarily have been prepared from the batch referred to.

Where reference is made to the use of a "similar" or "analogous" procedure, as will be appreciated by those skilled in the art, such a procedure may involve minor variation, for example reaction temperature, reagent/solvent amount, reaction time, work-up conditions or chromatographic purification conditions.

All temperatures refer to ° C.

In the Intermediates and Examples unless otherwise stated:

Proton Magnetic Resonance (NMR) spectra may be recorded on Bruker Avance II instruments at 300 or 400 MHz, chemical shifts are reported in ppm (δ) using the residual solvent line as internal standard. Splitting patterns are designed as s, singlet; d, doublet; t, triplet; q, quartet; m, multiplet; b, broad. The NMR spectra may be recorded at temperature ranging from 25 to 90° C.; when more than one conformer is detected, the chemical shifts for the most abundant one is reported.

Mass spectra (MS) may be taken on an ion-trap Finnigan MS LCQ, operating in ES (+) and ES (−) ionization mode.

LCMS may be taken on a quadrupole Mass Spectrometer on a Shimadzu lcms 2010 or Agilent LC/MSD 1100 Series, operating in ES (+) and ES (−) ionization mode.

(GC-MS) may be taken on a Shimadzu 2010 GCMS with E1 ion source (Column: DB-5 Carrier gas: He).

LC/MS-ES (+): analysis may be performed on YMC ODS (50×2.0 mm, 5 µm) (mobile phase: from 90% [water+0.1% TFA] and 10% [CH3CN+0.1% TFA] to 20% [water+0.1% TFA] and 80% [CH3CN+0.1% TFA] in 2.5 min, finally under these conditions for 0.5 min;

T=50° C.; flux=1.0 mL/min;

LC/MS-ES (−): analysis may be performed on YMC ODS (50×2.0 mm, 5 µm) (mobile phase: from 90% [water+0.1% TFA] and 10% [CH3CN+0.1% TFA] to 20% [water+0.1% TFA] and 80% [CH3CN+0.1% TFA] in 3 min, finally under these conditions for 2 min;

T=50° C.; flux=1.0 mL/min.

HPLC (walk-up) may be taken on Shimadzu 20AB HPLC with PDA detector (column: YMC ODS 50×4.6 mm, 5 cm).

Mobile phase: 90% [water+0.1% TFA] and 10% [CH3CN+0.1% TFA] to 20% [water+0.1% TFA] and 80% [CH3CN+0.1% TFA] in 6 min, finally under these conditions for 2 min; T=40° C.; flux=3.0 mL/min T.L.C. (or TLC) refers to thin layer chromatography on 0.25 mm silica gel plates (60E-254 China National Medicines) and visualized with UV light.

P-TLC refers to preparative thin layer chromatography.

For phase separations performed by using microfiltration devices: phase separation cartridge with polypropylene frit by Whatman or Alltech. SCX means: SCX-cartridges (loading 0.75 mmol/g) by Varian.

Solutions may be dried over anhydrous sodium sulphate.

Preparative HPLC (P-HPLC) may be conducted on a Gilson instrument with a YMC C18 5.0 µm column (250 mm×20 mm) by the following methods:

A: eluting with TFA (0.1%)/CH3CN 30% to 60%, over a 20 minutes gradient with a flow rate of 14 ml/min.

Preparative HPLC (P-HPLC) may be conducted on a Gilson instrument with a Shiseido UG80 C18 5.0 µm column (100 mm×20 mm) by the following methods:

B: eluting with TFA (0.1%)/CH3CN 30% to 60%, over a 12 minutes gradient with a flow rate of 18 ml/min.

Methylene chloride and DMF may be redistilled over calcium hydride and tetrahydrofuran may be redistilled over sodium.

The following abbreviations are used in the text: PE=petroleum ether, EA=ethyl acetate, NaI=sodium iodide, THF=tetrahydrofuran, HCl=hydrochloride, K2CO3=potassium carbonate, NaOH=sodium hydroxide, DCM=dichloromethane, Et3N=triethylamine, MeOH (or CH3OH)=methanol, Et20=diethyl ether, KCN=potassium cyanide, TLC=thin layer chromatography, Boc2O=di-tert-butyl dicarbonate, NMP=1-methyl-2-pyrrolidinone, FC=Flash Chromatography, NaHCO3=sodium bicarbonate, AcOH=acetic acid, AcNH4=ammonium acetate, P:E=petroleum ether:ethyl acetate, PPA=Polyphoshoric acid, DMAP=N,N-dimethyl-4-aminopyridine.

Preparation 1: ethyl (2E/Z))-(5-bromo-2,3-dihydro-1H-inden-1-ylidene)(cyano)ethanoate (Prep1)

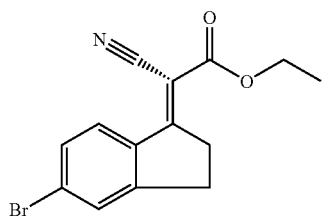

A mixture of 5-bromo-2,3-dihydro-1H-inden-1-one (5 g, 23.69 mmol, commercially available) and ethyl cyanoacetate (2.95 g, 27.8 mmol), ammonium acetate (3.65 g) and glacial acetic acid (10.85 mL) in benzene (24 mL) was refluxed with a Dean Stark water trap for 24 h. Then ethyl acetate was added to the reaction mixture and washed with water. The crude was purified by FC (cychloexane/ethyl acetate from 1/0 to 85/15) to give a still impure product that was crystallized from ethanol obtaining the compound 1 as a mixture of isomers (3.1 g, y=43%).

ES(MS) m/z: 307.2 (MH+).

Preparation 2: 5-bromo-1-(cyanomethyl)-2,3-dihydro-1H-indene-1-carbonitrile (Prep2)

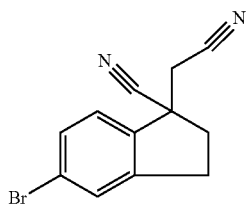

To a solution of ethyl (2E/Z))-(5-bromo-2,3-dihydro-1H-inden-1-ylidene)(cyano)ethanoate (Prep1, 3.1 g, 10.15 mmol) in ethanol (23 mL) a solution of KCN (1.65 g, 2.5 eq) in water (6 mL) was added and the reaction mixture was warmed to 65° C. and stirred for ~16-24 h. Then the solvent was removed under reduced pressure, the crude was treated with ether and water. Crystallization from ethanol gave the title compound (1.87 g, y=70%).

ES(MS) m/z: 262.2 (MH+).

Preparation 3: 5-bromo-2,3-dihydro-2'H,5'H-spiro[indene-1,3'-pyrrolidine]-2',5'-dione (Prep3)

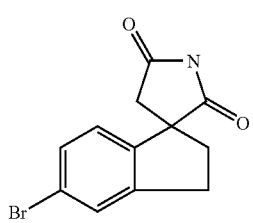

A mixture of compound 5-bromo-1-(cyanomethyl)-2,3-dihydro-1H-indene-1-carbonitrile (Prep2, 1.87 g) in glacial acetic acid (4 mL) and aqueous sulphuric acid (78% v/v, 1.4 mL) was warmed to 125° C. and stirred for 1.5 h. Then acetic acid was removed under reduced pressure and the residue treated with ethyl acetate and water. The crude product was purified by FC (eluting with cychloexane/ethyl acetate from 1/0 to 7/3) to give 0.4 of the title compound (y=20%).

ES(MS) m/z: 281.2 (MH+).

Preparation 4: 5-bromo-2,3-dihydrospiro[indene-1,3'-pyrrolidine] (Prep4)

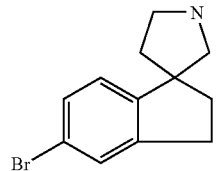

To a stirred solution of 5-bromo-2,3-dihydro-2'H,5'H-spiro[indene-1,3'-pyrrolidine]-2',5'-dione (Prep3, 0.4 g, 1.43 mmol) in anhydrous THF (8 mL), at 0° C. and under a nitrogen atmosphere, BH₃THF complex in THF (1M, 5.7 mL) was added dropwise. The ice-bath was removed, the reaction mixture was allowed to reach room temperature and then was refluxed for 6 h. The mixture was then cooled to 0° C. and hydrochloric acid (2 M, 5 mL) was cautiously added monitoring gas evolution, then the ice-bath was removed and the reaction stirred for 0.5 h. THF was then removed in vacuo, the residue was cooled to 0° C., dichloromethane was added and the stirred mixture was treated with a solution of NaOH (2M) until pH ~9. The mixture was extracted with additional DCM, the solvent evaporated under vacuum, the crude product was purified by FC (eluting with DCM/methanol from 1/0 to 94/6) to give the title compound (160 mg, y=45%).

¹H NMR (500 MHz, DMSO-d₆) d ppm 1.71-1.94 (m, 3H) 1.97-2.10 (m, 1H) 2.66 (d, 1H) 2.75-2.87 (m, 3H) 2.88-3.03 (m, 2H) 7.18 (d, 1H) 7.31 (d, 1H) 7.37 (br. s., 1H)

Preparation 5: (E)-ethyl 2-(5-chloro-2,3-dihydro-1H-inden-1-ylidene)-2-cyanoacetate (Prep5)

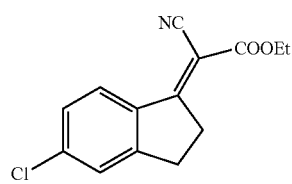

A mixture of 5-chloro-2,3-dihydro-1H-inden-1-one (150 g, 0.9 mol, commercially available) and ethyl cyanoacetate (125 g, 1.1 mol), ammonium acetate (150 g, 1.94 mmol) and glacial acetic acid (500 mL) in benzene (1 L) was refluxed with a Dean Stark water trap for 22 h. Then benzene was partially removed under vacuum, the residue was filtered and the solid obtain was crystallized from ethanol to give the title compound (161 g, y=68%).

¹H NMR (DMSO-d₆) δ: 1.20-1.30 (3H, t), 3.04-3.21 (3H, m), 3.41-3.49 (2H, m), 4.21-4.31 (2H, q), 7.50-7.57 (1H, d), 7.67-7.69 (1H, s), 8.37-8.40 (1H, d).

Preparation 6: 5-chloro-1-(cyanomethyl)-2,3-dihydro-1H-indene-1-carbonitrile (Prep6)

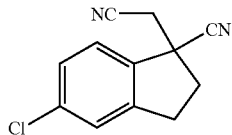

To a solution of (E)-ethyl 2-(5-chloro-2,3-dihydro-1H-inden-1-ylidene)-2-cyanoacetate (Prep5, 100 g, 0.38 mol) in ethanol (800 ml) a solution of KCN (67.5 g, 1 mol) in water (230 ml) was added and the reaction mixture was warmed to 65° C. and stirred for 21 h. Then the solvent was removed under vacuum The residue was treated with ether and the organic phase washed with water. Solvent was evaporated and the crude obtained was purified by crystallization from ethanol to obtain the title compound (36 g, y=43.5%).

$^1$H NMR (DMSO-d$_6$) δ: 2.34-2.41 (1H, m), 2.61-2.69 (1H, m), 2.97-3.12 (2H, m), 3.33-3.53 (2H, q), 7.38 (1H, d), 7.42 (1H, s), 7.57 (1H, m).

Preparation 7: 5-chloro-2,3-dihydrospiro[indene-1,3'-pyrrolidine]-2',5'-dione (Prep7)

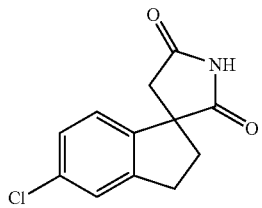

A mixture of 5-chloro-1-(cyanomethyl)-2,3-dihydro-1H-indene-1-carbonitrile (Prep6, 16 g, 74 mmol) in glacial acetic acid (30 ml) and aqueous sulphuric acid (78% v/v, 15 mL) was warmed to 110° C. and stirred for 1.5 h. Then acetic acid was removed under vacuum and the residue was treated with ethyl acetate and the organic phase washed with water. Solvent was evaporated and the crude material obtained was purified by crystallization from ethanol to obtain the title pure compound (4 g, y=23%)

$^1$H NMR (MeOD) δ: 2.11-2.18 (1H, m), 2.56-2.71 (1H, m), 2.88-2.98 (3H, m), 3.11-3.30 (1H, m), 6.97-6.99 (1H, d), 7.10-7.21 (2H, m).

Preparation 8: 5-chloro-2,3-dihydrospiro[indene-1,3'-pyrrolidine] (Prep8)

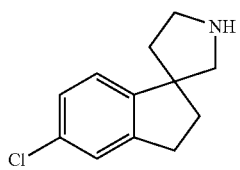

To a stirred solution of 5-chloro-2,3-dihydrospiro[indene-1,3'-pyrrolidine]-2',5'-dione (Prep7, 3 g, 12.7 mmol) in anhydrous THF (20 ml) at 0° C. and under a nitrogen atmosphere, BH$_3$(CH$_3$)$_2$S complex in THF (1M, 50 ml) was added dropwise. The ice-bath was removed, the reaction mixture was allowed to reach room temperature and refluxed for 28 h. The mixture was then cooled to 0° C. and hydrochloric acid (2 M, 30 ml) was cautiously added monitoring gas evolution, then the ice-bath was removed and the reaction was stirred for 1 h. THF was then removed in vacuo, the residue was cooled to 0° C. DCM was added and the stirred mixture was treated with a solution of NaOH (2M) until pH=13. The mixture was extracted with additional DCM, the solvent was evaporated under vacuum to obtain the crude title compound (3 g).

$^1$H NMR (CDCl3) δ: 1.25 (2H, t), 2.05-2.35 (2H, m), 2.94 (2H, m), 3.15-3.50 (4H, m), 7.20 (3H, m).

Preparation 9: tert-butyl 5-chloro-2,3-dihydrospiro[indene-1,3'-pyrrolidine]-1'-carboxylate (Prep9)

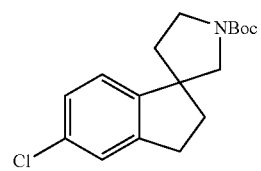

To a stirred solution of crude 5-chloro-2,3-dihydrospiro[indene-1,3'-pyrrolidine] (Prep8, 3 g, 14.5 mmol) in anhydrous dichloromethane (20 ml), (Boc)$_2$O (3.78 g, 17.4 mmol), Et$_3$N (5 ml, 36 mmol) and DMAP (catalityc amount) were added and the mixture was stirred overnight at room temperature. Then the solvent was removed in vacuo, the crude product was purified by FC (eluting with ethyl acetate/PE from 1:20 to 1:15) to give the title compound (0.9 g).

$^1$H NMR (CDCl3) δ: 1.45 (9H, m), 1.80-1.90 (1H, m), 1.97-2.20 (3H, m), 2.90 (2H, m), 3.30-3.70 (4H, m), 7.05 (1H, m), 7.15 (2H, m)

Preparation 10: 5-chloro-2,3-dihydrospiro[indene-1,3'-pyrrolidine]hydrochloride salt (Prep10)

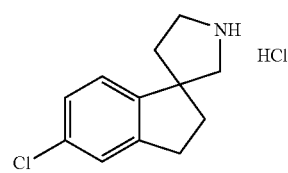

To a solution of tert-butyl 5-chloro-2,3-dihydrospiro[indene-1,3'-pyrrolidine]-1'-carboxylate (Prep9, 900 mg, 2.93 mol) in methanol (10 ml), HCl/CH$_3$OH (10 ml, 3M in methanol) was added and stirred overnight at room temperature. The solvent was evaporated in vacuo to give the title compound (500 mg, y=82%).

¹H NMR (CDCl3) δ: 2.00-2.25 (3H, m), 2.26-2.40 (1H, m), 2.85-2.95 (2H, m), 3.20-3.50 (3H, m), 3.51-3.66 (1H, m), 7.10-7.19 (3H, m).

Preparation 11: (E)-ethyl 2-cyano-2-(5-fluoro-2,3-dihydro-1H-inden-1-ylidee)acetate (Prep11)

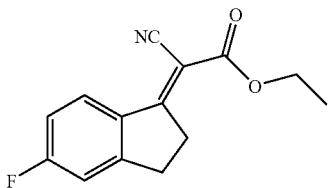

A mixture of 5-Fluoro-indan-1-one (150 g, 1 mol, commercially available), and ethyl cyanoacetate (125 g, 1.1 mol), ammonium acetate (154 g, 2 mol) and glacial acetic acid (500 ml) in benzene (1 L) was refluxed with a Dean Stark water trap for 16 h. Then ethyl acetate was added to the reaction mixture and washed with water.

The crude was purified by FC (EA/PE=1/3) to give the title compound that was further purified by crystallization from ethanol to obtain the title compound as brown solid (206 g, y=84.08%).

¹H NMR (DMSO-$d_6$) δ: 8.43-8.47 (1H, q), 7.40-7.43 (1H, d), 7.31-7.36 (1H, m), 4.21-4.26 (2H, q), 3.41-3.44 (2H, t), 3.05-3.08 (2H, t), 1.25-1.29 (3H, t).

Preparation 12: 1-(cyanomethyl)-5-fluoro-2,3-dihydro-1H-indene-1-carbonitrile (Prep12)

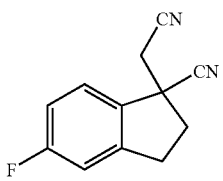

To a solution of (E)-ethyl 2-cyano-2-(5-fluoro-2,3-dihydro-1H-inden-1-ylidene)acetate (Prep11, 100 g, 0.408 mol) in ethanol (800 ml) a solution of KCN (67 g, 1.02 mol) in water (240 ml) was added, and warmed to 65° C. The mixture was stirred for 24 h.

The solvent was removed under vacuum. The residue was treated with ether and the organic phase washed with water. Solvent was evaporated and the crude material obtained was purified by crystallization from ethanol to obtain the title compound (60 g, y=73.5%).

¹H NMR (CDCl3) δ: 7.45-7.48 (1H, m), 7.00-7.06 (2H, m), 3.71 (2H, m), 2.97 (2H, d), 2.79-2.88 (1H, m), 2.45-2.52 (1H, m).

Preparation 13: 5-fluoro-2,3-dihydrospiro[indene-1,3'-pyrrolidine]-2',5'-dione (Prep13)

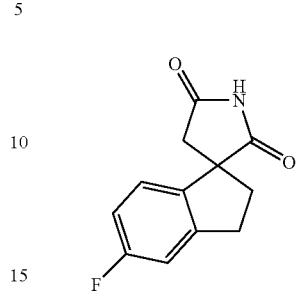

The mixture of 1-(cyanomethyl)-5-fluoro-2,3-dihydro-1H-indene-1-carbonitrile (Prep12, 60 g, 0.3 mol) in glacial acetic acid (170 ml) and aqueous sulfuric acid (78%, V/V, 58.6 ml) was warmed to 125° C., and stirred for 2 hours. Then acetic acid was removed under reduce pressure and the residue was treated with ethyl acetate and the organic phase washed with water. Solvent was evaporated and the crude material obtained was purified by FC (eluting with cyclohexane/EA from 1/0 to 7/3) to give the title compound as a white solid (26 g, y=40%).

¹H NMR (CDCl3) δ: 8.24 (1H, s), 6.89-7.08 (3H, m), 3.19-3.30 (1H, m), 2.90-3.05 (3H, m), 2.74-2.82 (1H, m), 2.17-2.27 (1H, m).

Preparation 14: 5-fluoro-2,3-dihydrospiro[indene-1,3'-pyrrolidine]hydrochloride salt (Prep14)

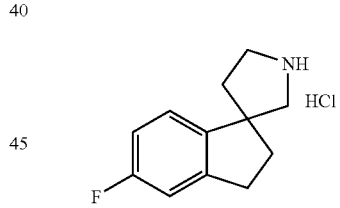

A solution of 5-fluoro-2,3-dihydrospiro[indene-1,3'-pyrrolidine]-2',5'-dione (Prep13, 5 g, 0.0227 mol) in THF (100 ml) was treated with 5 g of lithium aluminum hydride and heated to reflux for 16 h. With cooling in an ice bath, 3 ml of $H_2O$, 5 ml of 15% NaOH, and 10 ml $H_2O$ were added dropwise and stirred at room temperature for 1 h. After filtration and washing of the filtered cake with hot THF, the organic layers were combined and evaporated in vacuo, purified by FC (eluting with MeOH/EA=1/20 to 3/20) to give the title compound as free base (1 g 22.93%), which was treated with an excess of a 1N solution of HCl-Ether to obtain the corresponding hydrochloride salt (1.2 g).

¹H NMR (MeOD) δ: 7.29-7.34 (1H, m), 6.97-7.01 (2H, m), 3.58-3.62 (1H, m), 3.31-3.47 (3H, m), 2.97-3.02 (2H, m), 2.17-2.26 (4H, m).

ES(MS) m/z: 192 (MH+).

Preparation 15: 5-chloro-6-methoxy-2,3-dihydro-1H-inden-1-one (Prep15)

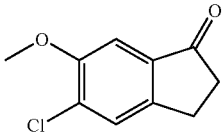

A solution of 3-(3-chloro-4-methoxyphenyl)propanoic acid (10 g, 46.7 mmol, commercially available) in PPA (100 mL) was stirred for 2 h at 70 C. Water was added to the mixture and extracted with EA twice. The organic phase were combined and dried over anhydrous $Na_2SO_4$, concentrated, purified by FC to afford 6 g of the title compound (y=66%).

$^1$H NMR (CDCl3) δ: 7.50 (1H, s), 7.23 (1H, s), 3.87-3.93 (3H, s), 3.05-3.08 (2H, t), 2.70-2.73 (2H, t).

Preparation 16: (E)-ethyl 2-(5-chloro-6-methoxy-2,3-dihydro-1H-inden-1-ylidene)-2-cyanoacetate (Prep16)

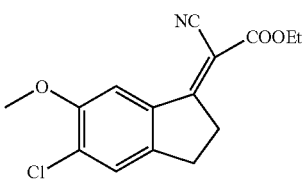

To the solution of 5-chloro-6-methoxy-2,3-dihydro-1H-inden-1-one (Prep15, 12 g, 61.2 mmol) in toluene (240 ml) was added ethyl cyanoacetate (8.3 g, 73.46 mmol), AcOH (48 ml, 0.8 mol) and ammonium acetate (12 g, 0.16 mol). The mixture was stirred for 12 hours at 120° C., checked by TLC, concentrated, filtered and washed with water and ethanol twice and purified by FC to afford 11 g of title compound (y=62%).

$^1$H NMR (DMSO-d$_6$) δ: 8.13 (1H, s), 7.72 (1H, s), 4.20-4.32 (2H, q), 3.87 (3H, s), 3.40-3.48 (2H, m), 3.01-3.05 (2H, m), 1.28-1.29 (3H, t).

Preparation 17: 5-chloro-1-(cyanomethyl)-6-methoxy-2,3-dihydro-1H-indene-1-carbonitrile (Prep17)

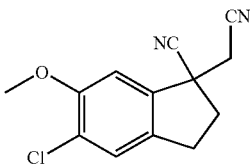

To a solution of (E)-ethyl 2-(5-chloro-6-methoxy-2,3-dihydro-1H-inden-1-ylidene)-2-cyanoacetate (Prep16, 6.02 g, 24.4 mmol) in ethanol (25 ml) was added a solution of KCN (3.61 g, 60 mmol) in water. The mixture was stirred for one day at 65-70° C. Water was added and extracted with ethyl acetate twice. The organic phases were combined and dried over anhydrous $Na_2SO_4$, concentrated and purified by FC to afford the title compound (800 mg, y=16%).

$^1$H NMR (CDCl3) δ: 7.31 (1H, s), 7.04 (1H, s), 3.93 (3H, s), 2.95-3.12 (2H, m), 2.91 (2H, s), 2.75-2.88 (1H, m), 2.41-2.50 (1H, m).

Preparation 18: 5-chloro-6-methoxy-2,3-dihydrospiro[indene-1,3'-pyrrolidine]-2',5'-dione (Prep18)

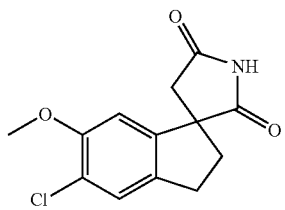

To a solution of 5-chloro-1-(cyanomethyl)-6-methoxy-2,3-dihydro-1H-indene-1-carbonitrile (Prep17, 520 mg, 2.11 mmol) in AcOH (5.2 ml), $H_2SO_4$ (0.364 ml) was added. The mixture was stirred for 15 min at 200° C. Water was added and the mixture extracted with EA twice, solvent was evaporated, dried over $Na_2SO_4$, concentrated to give the title compound that was used in the next step without further purification. (540 mg, y=96%).

$^1$H NMR (DMSO) δ: 11.28 (1H, s), 7.34 (1H, s), 7.05 (1H, s), 3.83 (3H, s), 2.81-3.05 (4H, m), 2.10-2.70 (2H, m).

Preparation 19: 5-chloro-6-methoxy-2,3-dihydrospiro[indene-1,3'-pyrrolidine](Prep19)

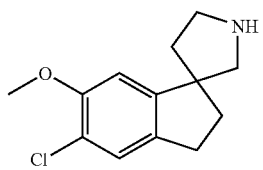

To a solution of 5-chloro-6-methoxy-2,3-dihydrospiro[indene-1,3'-pyrrolidine]-2',5'-dione (Prep18, 540 mg, 2.04 mmol) in THF (18 ml) cooled to 0° C., BH$_3$-THF (8.15 ml, 8.15 mmol, 1M in THF) was added under argon. The mixture was stirred for one day at 80° C. A 1N solution of HCl was added and stirred for 30 min, concentrated to remove THF and extracted with $CH_2Cl_2$ twice. The organic phases were concentrated, evaporated and the crude purified by FC to afford 250 mg of the title compound (y=51%).

$^1$H NMR (CDCl3) δ: 7.19 (1H, s), 6.75 (1H, s), 3.83 (3H, s), 2.68-3.21 (6H, m), 1.80-2.20 (4H, m).

Preparation 20: 2,4-bis(benzyloxy)-5-bromopyrimidine (Prep20)

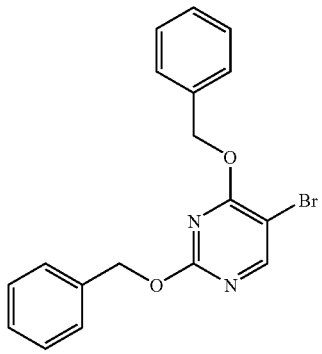

To a suspension of sodium hydride (31.25 g, 0.8 mol) in toluene (1500 ml) benzyl alcohol was added dropwise (57.5 g, 0.53 mol) in ice-bath, and the mixture was stirred at 0° C. for 1 hour, then a solution of 5-bromo-2,4-dichloropyrimidine (50 g, 0.22 mol) in toluene (100 ml) was added dropwise. The resulting solution was stirred overnight. After concentration, the residue was recrystallized with ethyl acetate to give the pure title compound (60 g, y=73.3%).

$^1$H NMR (DMSO) δ: 5.34 (2H, s), 5.47 (2H, s), 7.33-7.46 (10H, m), 8.55 (1H, s).

Preparation 21: 4-bis(benzyloxy)-5-(thiophen-2-yl)pyrimidine (Prep21)

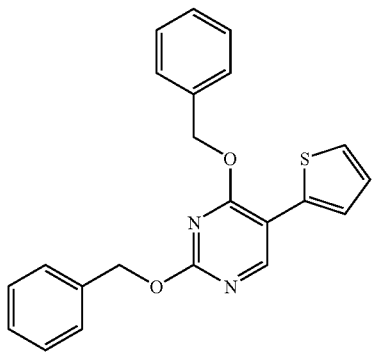

The mixture of 2,4-bis(benzyloxy)-5-bromopyrimidine (Prep20, 60 g, 0.16 mol), 2-thienylboronic acid (81.7 g, 0.64 mol), Tetrakis(triphenylphosphine)palladium (18.5 g, 0.02 mol), sodium carbonate (34 g, 0.32 mol) was degassed three times. Then water (600 ml) and 1,4-dioxane (1800 ml) were added quickly. The resulting mixture was degassed, and the reaction mixture was heated to 110° C. under nitrogen for 4 hours. After cooling to room temperature, water and ethyl acetate were added. The aqueous was extracted three times with ethyl acetate and the combined organic layer was dried and concentrated. The residue was purified by column (P:E=10:1) to afford the title compound (20 g; y=33%).

$^1$H NMR (DMSO) δ: 5.43 (2H, s), 5.55 (2H, s), 7.10-7.13 (1H, m), 7.34-7.58 (12H, m), 8.77 (1H, s).

Preparation 22: 5-(thiophen-2-yl)pyrimidine-2,4(1H,3H)-dione (Prep22)

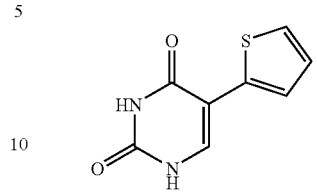

To a solution of 2,4-bis(benzyloxy)-5-(thiophen-2-yl)pyrimidine (Prep21, 20 g, 53.5 mol) in dry dichloromethane (400 ml), iodotrimethylsilane (28.8 g, 0.14 mol) was added at room temperature. The resulting solution was stirred for 3 hours. Then methanol was added, the precipitate was filtered and the solid was recrystallized with methanol twice, to afford 7 g of the title compound (y=67.3%)

$^1$H NMR (DMSO) δ: 7.01-7.04 (1H, m), 7.39-7.41 (1H, m), 7.45-7.46 (1H, m), 7.95-7.97 (1H, d), 11.25 (1H, d), 11.41 (1H, s).

Preparation 23: 1-(4-chlorobutyl)-5-(thiophen-2-yl)pyrimidine-2,4(1H,3H)-dione (Prep23)

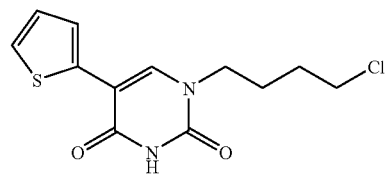

The solution of 5-(thiophen-2-yl)pyrimidine-2,4(1H,3H)-dione (Prep22, 2.5 g, 12.9 mmol), 1-bromo-4-chlorobutane (2.2 g, 12.9 mmol) and potassium carbonate (1.8 g, 12.9 mmol) in DMF (150 ml) was stirred at room temperature for 5 hours. Water was added and the solution was adjusted to pH=6 with 3N hydrochloride acid. Ethyl acetate was added and the aqueous layer was extracted three times, the combined organic layer was dried and concentrated, the residue was purified by FC(P:E=3:1) to give the title compound (800 mg, y=22%).

$^1$H NMR (DMSO) δ: 1.62-1.85 (4H, m), 3.63-3.66 (2H, m), 3.77-3.82 (2H, m), 7.01-7.04 (1H, t), 7.23-7.24 (1H, d), 7.38-7.40 (1H, d), 8.32 (1H, s), 11.60 (1H, s).

Preparation 24: 1-(3-chloropropyl)-5-(thiophen-2-yl)pyrimidine-2,4(1H,3H)-dione (Prep24)

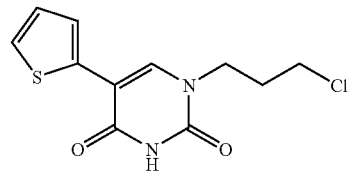

A mixture of 5-(thiophen-2-yl)pyrimidine-2,4(1H,3H)-dione (Prep22, 1 g, 5.15 mmol), 1-bromo-3-chloropropane (0.81 g, 5.15 mmol) and potassium carbonate (0.71 g, 5.15 mmol) in DMF (10 ml) was stirred at room temperature for 7 hours, then the mixture was diluted with water and extracted with ethyl acetate. Organic phase was evaporated and the crude was purified by a FC (eluent P:E=3:1, 1:1) to afford the title compound (300 mg, y=21%)

$^1$H NMR (DMSO) δ: 2.09-2.14 (2H, m), 3.67-3.71 (2H, t), 3.86-3.91 (2H, t), 7.04-7.07 (1H, t), 7.43-7.46 (2H, m), 8.25 (1H, s), 11.61 (1H, s).

Preparation 25: ethyl 2,4-dimethylthiazole-5-carboxylate (Prep25)

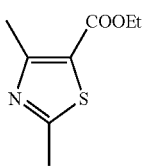

The mixture of ethyl 2-chloroacetoacetate (111.2 g, 0.68 mol) and thioacetamide (40 g, 0.68 mol) in 150 ml ethanol was heated to 90° C. and stirred for 5 h. After cooling to room temperature, the solvent was removed under vacuum to afford the title compound (105 g, y=83%).

$^1$H NMR (MeOD) δ: 1.35-1.41 (3H, t), 2.75 (3H, s) 2.94 (3H, s), 4.40 (2H, q).

Preparation 26: 2,4-dimethylthiazole-5-carbohydrazide (Prep26)

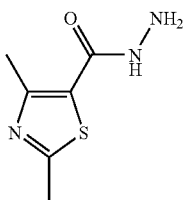

To ethyl 2,4-dimethylthiazole-5-carboxylate (Prep25, 50 g, 0.27 mol) in ethanol (200 mL), hydrazine hydrate (64 g, 1.08 mol) was added. The mixture was stirred at 90° C. overnight. After cooling to room temperature, the solvent was removed under vacuum to afford 41 g of crude product as a solid. The crude was purified by FC to give 23 g pure title compound product (y=50%).

$^1$H NMR (DMSO) δ: 2.54 (3H, s), 2.63 (3H, s), 4.51 (2H, s), 9.45 (1H, s).

Preparation 27: 5-(2,4-dimethylthiazol-5-yl)-4-methyl-4H-1,2,4-triazole-3-thiol (Prep27)

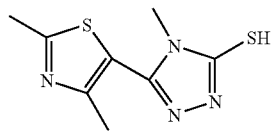

To a 2,4-dimethylthiazole-5-carbohydrazide (Prep26, 23 g, 0.13 mol) in ethanol (100 ml), methyl isothiocyanate (49.1 g, 0.67 mol) was added. The mixture was refluxed overnight. Then the ethanol was partially removed under vacuum and the residue was filtered. The solid was dried under vacuum to afford 14 g of the title compound (y=46%).

$^1$H NMR (DMSO) δ: 2.27 (3H, s), 2.63 (3H, s), 3.42 (3H, s), 14.05 (1H, s)

Preparation 28: 5-(5-(3-chloropropylthio)-4-methyl-4H-1,2,4-triazol-3-yl)-2,4-dimethylthiazole (Prep28)

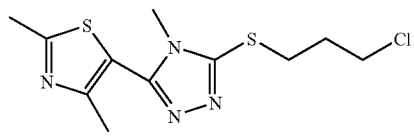

5-(2,4-dimethylthiazol-5-yl)-4-methyl-4H-1,2,4-triazole-3-thiol (Prep27, 5 g, 22 mmol) was added to a mixture of methanol (15 ml) and acetone (35 ml), followed by $K_2CO_3$ (5 g, 36 mmol) and 1-bromo-3-chloropropane (35 ml, 36 mmol). The suspension was stirred at 22° C. for 24 h. The volume of solvent was reduced, then ethyl acetate (63 ml) was added and the organic layer was washed with water, the EA was removed under vacuum and the crude purified by FC (EA/MeOH 15:1) to afford 2.5 g of pure product (y=37%).

$^1$H NMR (DMSO) δ: 2.09-2.20 (2H, m), 2.34 (3H, s), 2.68 (3H, s), 3.21 (2H, t), 3.46 (3H, s), 3.76 (2H, t).

The following spiroamines were prepared according to a similar sequence of procedures to that described above in Prep1 to Prep4 starting from commercially available ketones (shown in the table below):

| Prep | Structure | Name | Starting material | Overall Yield (%) |
|---|---|---|---|---|
| 30 | 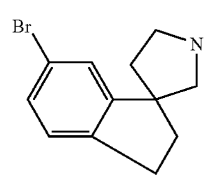 | 6-bromo-2,3-dihydrospiro[indene-1,3'-pyrrolidine] | | 2.6 |

| Prep | Structure | Name | Starting material | Overall Yield (%) |
|---|---|---|---|---|
| 31 | 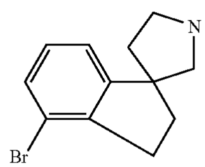 | 4-bromo-2,3-dihydrospiro[indene-1,3'-pyrrolidine] | | 5.7 |
| 32 | 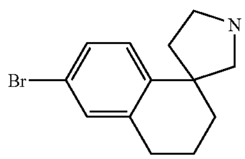 | 6-bromo-3,4-dihydro-2H-spiro[naphthalene-1,3'-pyrrolidine] | | 2.0 |
| 33 | 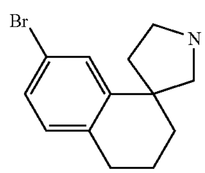 | 7-bromo-3,4-dihydro-2H-spiro[naphthalene-1,3'-pyrrolidine] | | 1.8 |
| 34 | 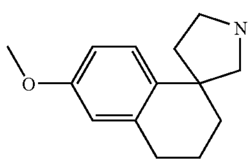 | 6-(methyloxy)-3,4-dihydro-2H-spiro[naphthalene-1,3'-pyrrolidine] | | 10 |
| 35 | 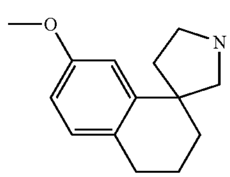 | 7-(methyloxy)-3,4-dihydro-2H-spiro[naphthalene-1,3'-pyrrolidine] | | 15 |
| 36 | 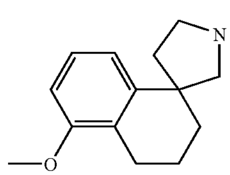 | 5-(methyloxy)-3,4-dihydro-2H-spiro[naphthalene-1,3'-pyrrolidine] | | 13 |
| 37 | 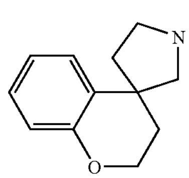 | 2,3-dihydrospiro[chromene-4,3'-pyrrolidine] | | 3 |

Prep 38: (E)-ethyl 2-(6-chloro-2,3-dihydro-1H-inden-1-ylidene)-2-cyanoacetate (Prep38)

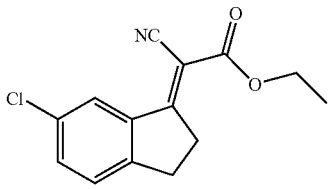

To a solution of 6-chloro-indan-1-one (commercially available, 16 g, 0.1 mol) in Benzene (500 ml), AcOH (160 ml) CH$_3$COONH$_4$ (80 g) and ethyl cyanoacetate (14.4 g, 0.13 mol) were added. The mixture was heated to 100° C. and stirred overnight with a Dean stark water trap. Then ethyl acetate was added and the mixture washed with water. The residue was first purified by FC followed by crystallization from ethanol to obtain the title compound (16.2 g, y=64.5%).

$^1$H NMR (DMSO) δ: 8.42 (1H, s), 7.69-7.72 (1H, d), 7.62-7.64 (1H, d), 4.25-4.30 (2H, q), 3.46-3.48 (2H, t), 3.06-3.08 (2H, t), 1.27-1.31 (3H, t).

Preparation 39: 6-chloro-1-(cyanomethyl)-2,3-dihydro-1H-indene-1-carbonitrile (Prep39)

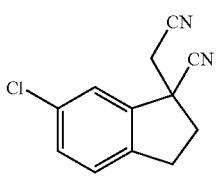

A solution of (E)-ethyl 2-cyano-2-(6-chloro-2,3-dihydro-1H-inden-1-ylidene)acetate (Prep38, 15.00 g, 0.06 mol) in ethanol (300 ml) was treated with a solution of KCN (9.75 g, 0.15 mol) in water (90 ml). The mixture was warmed to 65° C., and stirred for 16 h. The mixture was concentrated in vacuo to remove solvent. The residue was extracted with EA (100 ml×3). The organic layers were combined and washed with a saturated solution of NaHCO$_3$, brine and dried over Na$_2$SO$_4$. The crude was purified by FC (P:E=10/1) to obtain the title compound (4.60 g, y=37.1%).

$^1$H NMR (CDCl3) δ: 7.40 (1H, s), 7.27-7.30 (1H, d), 7.17-7.19 (1H, d), 3.01-3.06 (2H, m), 2.81-2.94 (2H, q), 2.71-2.78 (1H, m), 2.39-2.46 (1H, m).

Preparation 40: 6-chloro-2,3-dihydrospiro[indene-1,3'-pyrrolidine]-2',5'-dione (Prep40)

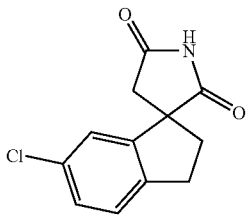

The mixture of 1-(cyanomethyl)-6-chloro-2,3-dihydro-1H-indene-1-carbonitrile (Prep. 39, 250 mg, 1.16 mmol), and AcOH (2.5 ml), H$_2$SO$_4$ (78%, 0.18 ml) was heated to 125° C. The mixture was stirred overnight at 125° C.

The mixture was quenched with water and extracted with EA (10 ml×3). The organic layers were combined and washed with Sat. NaHCO$_3$, brine, and dried over Na$_2$SO$_4$. The organic phase was concentrated in vacuo to obtain the title compound (250 mg, y=93.9%).

$^1$H NMR (CDCl3) δ: 8.30 (1H, b), 7.17-7.19 (2H, m), 7.16 (1H, s), 3.10-3.18 (1H, m), 2.78-2.95 (2H, m), 2.66-2.73 (1H, m), 2.11-2.19 (2H, m).

Preparation 41: 6-chloro-2,3-dihydrospiro[indene-1,3'-pyrrolidine](Prep41)

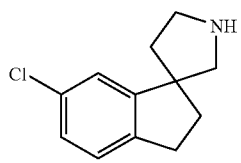

A solution of 6-chloro-2,3-dihydrospiro[indene-1,3'-pyrrolidine]-2',5'-dione (Prep. 40 250 mg, 1.06 mmol) in THF (10 ml) was treated with BH$_3$THF (1M, 10.6 ml, 10.6 mmol). The mixture was heated to refluxed and stirred for 48 hours.

The mixture was cooled to 0° C., and 2N HCl (5 ml) was added. The mixture was stirred at room temperature for 1 hour. The mixture was concentrated in vacuo to remove solvent. The residue was diluted with DCM (10 ml), and treated with NaOH to pH=10. The mixture was extracted with DCM (10 ml×3). The organic layers were washed with Sat. NaHCO$_3$, brine and dried over Na$_2$SO$_4$. The organic layer was concentrated in vacuo to get the title compound that was used in the next step without further purification (200 mg).

ES(MS) m/z 208 (MH$^+$)

Preparation 42: tert-butyl 6-chloro-2,3-dihydrospiro[indene-1,3'-pyrrolidine]-1'-carboxylate (Prep42)

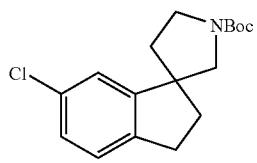

The mixture of 6-chloro-2,3-dihydrospiro[indene-1,3'-pyrrolidine] (Prep 41, 200 mg, 0.97 mmol), (Boc)$_2$O (340 mg, 1.56 mmol), DMAP (10 mg), and Et$_3$N (300 mg, 3 mmol) in DCM (10 ml) was stirred overnight at room temperature.

The mixture was purified by FC (PE/EA=30/1) to get the title compound (80 mg, y=27%).

¹H NMR (MeOD) δ: 7.15-7.20 (3H, m), 3.50-3.61 (1H, m), 3.30-3.48 (3H, m), 2.90-2.93 (2H, m), 2.06-2.16 (3H, m), 1.95-1.99 (1H, m), 1.47-1.50 (9H, d).

Preparation 43: 6-chloro-2,3-dihydrospiro[indene-1, 3'-pyrrolidine]hydrochloride (Prep43)

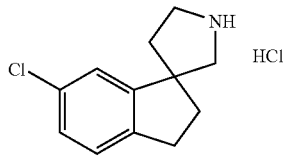

To a solution of tert-butyl 6-chloro-2,3-dihydrospiro[indene-1,3'-pyrrolidine]-1'-carboxylate (Prep42, 2.50 g, 8.14 mmol) in ether (50 ml), a 1N solution of hydrochloric acid-ether (50 ml) was added and stirred overnight. The mixture was washed by anhydrous ether. The residue was dissolved in DCM and concentrated to give the title compound (1.8 g, y=81.3%).
¹H NMR (MeOD) δ: 7.35 (1H, s), 7.24 (2H, s), 3.54-3.61 (1H, m), 3.34-3.48 (3H, m), 2.92-2.98 (2H, m), 2.12-2.26 (4H, m).
ES(MS) m/z 208 (MH⁺)
HPLC: 98.97%.

Preparation 44: (E)-ethyl 2-cyano-2-(6-fluoro-2,3-dihydro-1H-inden-1-ylidene)acetate (Prep44)

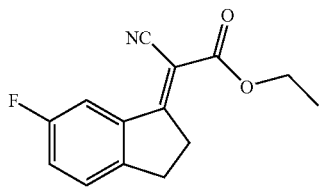

The mixture of compound 6-Fluoro-indan-1-one (5 g, 0.03 mol), and ethyl cyanoacetate (5 g, 0.05 mol), ammonium acetate (25 g, 0.33 mol) and glacial acetic acid (50 ml) in toluene (205 ml) was refluxed with a Dean Stark water trap for 4 h. The mixture was concentrated in vacuo, the residue washed by water and EtOH three times to afford the the compound (8.00 g, y=97.96%).
¹H NMR (DMSO) δ: 8.09-8.13 (1H, dd), 7.59-7.62 (1H, m), 7.47-7.55 (1H, m), 4.22-4.30 (2H, q), 3.45-3.48 (2H, m), 3.03-3.06 (2H, t), 1.26-1.30 (3H, t).

Preparation 45: 1-(cyanomethyl)-6-fluoro-2,3-dihydro-1H-indene-1-carbonitrile (Prep45)

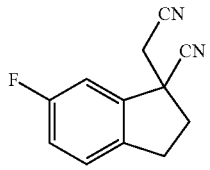

To a solution of (E)-ethyl 2-cyano-2-(6-fluoro-2,3-dihydro-1H-inden-1-ylidene)acetate (Prep44, 7.5 g, 0.03 mol) in ethanol (100 ml), a solution of KCN (4.65 g, 0.08 mol) in water (30 ml) was added. The mixture was warmed to 65° C., and stirred for 7 h.
The mixture was concentrated in vacuo and extracted with EA. The organic layers were evaporated and the crude product was purified by FC(P:E=10/1) to obtain the title compound (2.30 g, y=37.57%).
¹H NMR (CDCl3) δ: 7.27-7.29 (1H, m), 7.18-7.20 (1H, d), 7.06-7.10 (1H, td), 3.07-3.12 (2H, m), 2.86-3.03 (2H, m), 2.79-2.84 (1H, m), 2.47-2.53 (1H, m).

Preparation 46: 6-fluoro-2,3-dihydrospiro[indene-1, 3'-pyrrolidine]-2',5'-dione (Prep46)

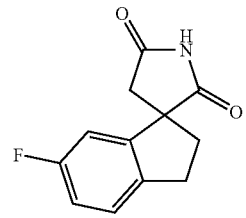

The mixture of 1-(cyanomethyl)-6-fluoro-2,3-dihydro-1H-indene-1-carbonitrile (Prep45, 2 g, 0.01 mol) in glacial acetic acid (20 ml) and aqueous sulfuric acid (78%, V/V, 1.4 ml) was warmed to 125° C., and stirred for 5 hours. The mixture was concentrated under reduced pressure to remove acetic acid. The residue was treated with EA and water. The organic phases were washed by Sat. NaHCO₃ and brine and dried over Na₂SO₄. The organic layer was concentrated in vacuo to afford the title compound (2 g, y=91.32%).
¹H NMR (CDCl3) δ: 8.96 (1H, s), 7.15-7.18 (1H, m), 6.87-6.90 (1H, m), 6.72-6.74 (1H, d), 3.10-3.15 (1H, m), 2.84-2.95 (3H, m), 2.66-2.73 (1H, m), 2.11-2.18 (1H, m).

Preparation 47: 6-fluoro-2,3-dihydrospiro[indene-1, 3'-pyrrolidine](Prep47)

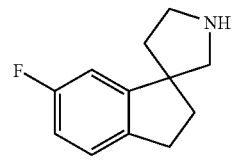

At 0° C., BH₃-THF (36.6 ml, 36.6 mmol) was added dropwise to a solution of 6-fluoro-2,3-dihydrospiro[indene-1,3'-pyrrolidine]-2',5'-dione (Prep46, 2 g, 9.13 mmol) in anhydrous THF (40 ml). The ice bath was removed. Then the reaction mixture was warmed to reflux overnight.
The mixture was cooled to 0° C. Then 2M HCl was added to the mixture. The ice bath was removed, the mixture was stirred for 0.5 h at room temperature. THF was removed in vacuo. The residue was cooled to 0° C. DCM was added to the mixture. Then the mixture was treated with 2M NaOH up to pH>9. The mixture was extracted with DCM. The organic phase was washed with brine, dried over Na₂SO₄, and concentrated in vacuo to obtain the title compound (1.6 g, y=87.6%).

¹H NMR (DMSO) δ: 7.18-7.19 (1H, t), 7.10-7.13 (1H, d), 6.90-6.99 (1H, t), 3.10-3.20 (1H, m), 2.96-3.08 (2H, m), 2.89-2.92 (1H, m), 2.75-2.82 (2H, m), 2.05-2.12 (1H, m), 1.82-2.00 (3H, m).

Preparation 48: 1-(3-chloropropyl)-5-methyl-2,4(1H,3H)-pyrimidinedione (Prep48)

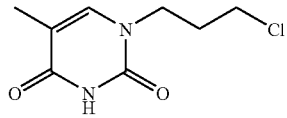

The title compound may be prepared according to the procedure described in Eur. Pat. Appl. (1996), EP748800 A2.

Preparation 49: 1-(4-chlorobutyl)-5-methyl-2,4(1H,3H)-pyrimidinedione (Prep49)

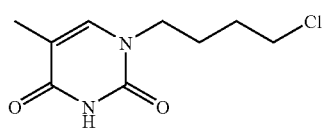

The title compound may be prepared according to the procedure described in Bioorganic & Medicinal Chemistry Letters (2006), 16(3), 490-494.

Preparation 50: 1-(5-chloropentyl)-5-methyl-2,4(1H,3H)-pyrimidinedione (Prep50)

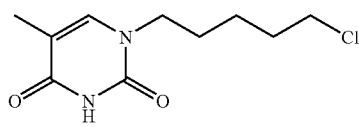

5-methyl-2,4(1H,3H)-pyrimidinedione (commercially available, 0.55 g, 3.97 mmol) was dissolved in dry DMF (15 mL). $K_2CO_3$ (0.548 g, 3.97 mmol) was added and the mixture stirred at room temperature for 1 hour. 1-bromo-5-chloropentane (0.526 ml, 3.97 mmol) was then added and the suspension was stirred at room temperature for 4 h. The volume of solvent was reduced, then DCM was added and the organic layer was washed with water, the organic phase was evaporated and the crude purified by FC (DCM/MeOH 98/2-95/5) to afford 0.1 g of the title compound (y=11%).

¹H NMR (CDCl3) δ: 8.69 (1H, bs), 6.99 (1H, s), 3.74 (2H, t), 3.56 (2H, t), 2.63 (3H, s), 1.84 (2H, m), 1.73 (2H, m), 1.53 (2H, m),

Example 1

5-bromo-1'-(3-{[3-(4-methyl-1,3-oxazol-5-yl)-1H-1,2,4-triazol-5-yl]thio}propyl)-2,3-dihydrospiro[indene-1,3'-pyrrolidine]hydrochloride (E1)

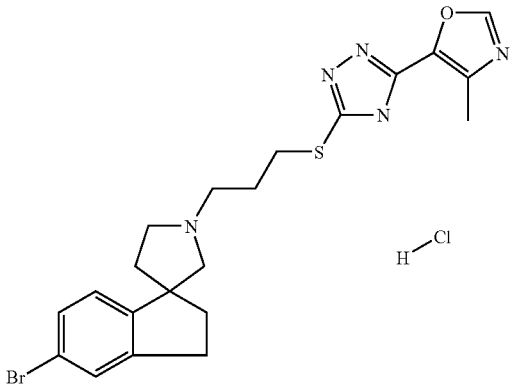

To a solution of 5-bromo-2,3-dihydrospiro[indene-1,3'-pyrrolidine] (Prep4, 0.04 g, 0.159 mmol) in dry DMF (1 ml), 3-[(3-chloropropyl)thio]-5-(4-methyl-1,3-oxazol-5-yl)-1H-1,2,4-triazole (reference procedure for preparation described in WO05/080382, 0.058 g, 0.213 mmol) was added. Then, $K_2CO_3$ (0.029 g) and NaI (0.028 g) were added and the mixture was heated at 80° C. for 24 hours. Water was then added and the solution was extracted with ethyl acetate. The organic phase was washed with brine, dried over $Na_2SO_4$ and concentrated in vacuo. The crude product was purified by a silica SPE cartridge eluting with dichloromethane/methanol from 100/0 to 98/to obtain 0.036 g of the title compound as free base. To a solution of this material in dichloromethane (1 mL) was added 0.073 mL of HCl (1M in $Et_2O$), the solvent was evaporated in vacuo and the material thus obtained triturated with $Et_2O$ to give 32 mg of the title compound as a white slightly hygroscopic solid.

¹H NMR (400 MHz, DMSO-$d_6$) d ppm 1.82-2.39 (m, 6H) 2.29-2.35 (m, 3H) 2.76-2.92 (m, 2H) 3.04-3.49 (m, 6H) 3.57-3.80 (m, 2H) 3.64 (s, 3H) 7.30-7.50 (m, 3H) 8.44-8.58 (m, 1H) 10.70 (br. s., 1H)

Example 2

5-(5-(3-(5-chloro-6-methoxy-2,3-dihydrospiro[indene-1,3'-pyrrolidine]-1'-yl)propylthio)-4-methyl-4H-1,2,4-triazol-3-yl)-2,4-dimethylthiazole hydrochloride (E2)

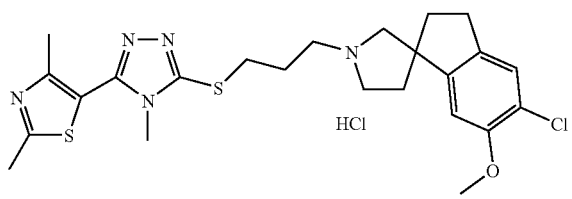

The mixture of 5-chloro-6-methoxy-2,3-dihydrospiro[indene-1,3'-pyrrolidine] (Prep19, 58 mg, 0.24 mmol), 5-(5-(3-chloropropylthio)-4-methyl-4H-1,2,4-triazol-3-yl)-2,4-dimethylthiazole (Prep28, 50 mg, 0.17 mmol), K$_2$CO$_3$ (68.5 mg, 0.50 mmol) and NaI (24.5 mg, 0.50 mmol) in NMP (1 ml) was warmed to 70° C., and stirred overnight. The mixture was extracted with EA (5 ml×2). The combined organic layers were washed with Sat. NaHCO$_3$, brine and dried over Na$_2$SO$_4$. The organic layer was concentrated in vacuo to afford crude product. The crude was purified by P-TLC and P-HPLC and treated with a 1N solution of HCl in ether, then freeze-dried to afford title compound (10 mg, y=11.98%).

$^1$H NMR (MeOD) δ: 7.16-7.31 (2H, m), 3.71-4.02 (5H, m), 3.58-3.69 (4H, m), 3.35-3.59 (5H, m), 2.90-2.95 (2H, m), 2.81 (3H, s), 2.41-2.63 (4H, m), 2.15-2.40 (5H, m).

ES(MS) m/z: 504 (MH$^+$).

Example 3

5-(5-(3-(5-chloro-2,3-dihydrospiro[indene-1,3'-pyrrolidine]-1'-yl)propylthio)-4-methyl-4H-1,2,4-triazol-3-yl)-2,4-dimethylthiazole (E3)

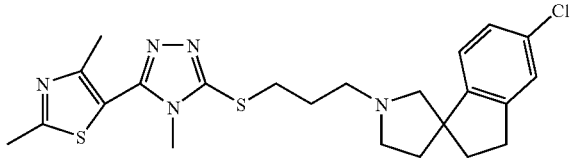

To a solution of 5-(5-(3-chloropropylthio)-4-methyl-4H-1,2,4-triazol-3-yl)-2,4-dimethylthiazole (Prep28, 70 mg, 0.23 mmol) in dry NMP (1 ml), K$_2$CO$_3$ (0.144 g, 1 mmol) was added and stirred for 10 min, then 5-chloro-2,3-dihydrospiro[indene-1,3'-pyrrolidine]hydrochloride (Prep10, 88 mg, 0.36 mmol) and NaI (0.07 g) were added and stirred for 23 h at 65° C. Water was then added and the solution was extracted with ethyl acetate (2×10 ml). The organic phase was washed with brine, dried over Na$_2$SO$_4$ and concentrated in vacuo. The crude product was purified by P-HPLC (TLC analysis performed by eluting with EA/MeOH 80:10) to give 57 mg of the title compound (y=52%).

$^1$H NMR (CDCl3) δ: 1.90-2.20 (6H, m), 2.42 (3H, s), 2.61-2.92 (11H, m), 3.31-3.42 (2H, t), 3.46 (3H, s), 7.10 (2H, m), 7.21 (1H, m).

Example 4

5-(5-(3-(5-chloro-2,3-dihydrospiro[indene-1,3'-pyrrolidine]-1'-yl)propylthio)-4-methyl-4H-1,2,4-triazol-3-yl)-2,4-dimethylthiazole hydrochloride (E4)

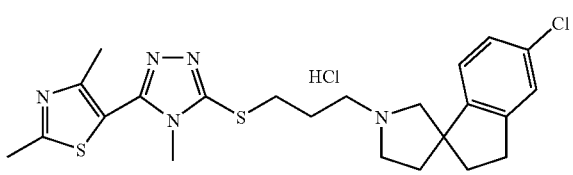

To a solution of 5-(5-(3-(5-chloro-2,3-dihydrospiro[indene-1,3'-pyrrolidine]-1'-yl)propylthio)-4-methyl-4H-1,2,4-triazol-3-yl)-2,4-dimethylthiazole (E3, 57 mg, 0.12 mmol) in Et$_2$O (3 ml) and methanol (0.5 ml), 10 ml of HCl/Ether (1M in Et$_2$O) were added, the solvent was evaporated in vacuo and treated with Et2O to give 50 mg of the title compound (y=82%).

$^1$H NMR (MeOD), δ: 2.10-2.40 (6H, m), 2.49 (3H, s), 2.84 (3H, s), 3.29 (2H, m), 3.40-3.60 (6H, m), 3.69 (3H, s), 3.75-4.00 (2H, m), 7.20-7.50 (3H, m).

Example 5

5-(5-(3-(5-fluoro-2,3-dihydrospiro[indene-1,3'-pyrrolidine]-1'-yl)propylthio)-4-methyl-4H-1,2,4-triazol-3-yl)-2,4-dimethylthiazole (E5)

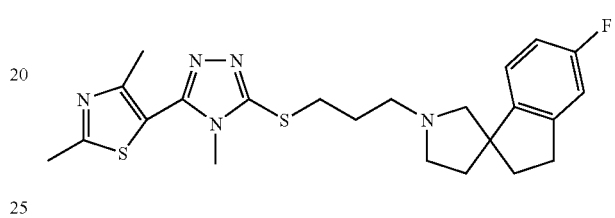

To a solution of 5-(5-(3-chloropropylthio)-4-methyl-4H-1,2,4-triazol-3-yl)-2,4-dimethylthiazole (Prep28, 70 mg, 0.23 mmol) in dry NMP (1 ml), K$_2$CO$_3$ (0.145 g, 1.05 mmol) was added and stirred for 10 min. Then 5-fluoro-2,3-dihydrospiro[indene-1,3'-pyrrolidine]hydrochloride salt (Prep14, 88 mg, 0.39 mmol) and NaI (0.07 g, 0.47 mmol) were added and stirred overnight at 65° C. Water was then added and the solution was extracted with ethyl acetate (2×10 ml). The organic phase was washed with brine, dried over Na$_2$SO$_4$ and concentrated in vacuo. The crude product was purified by P-HPLC to give 38 mg of the title compound (y=36%).

$^1$H NMR (CDCl3) δ: 1.90-2.30 (6H, m), 2.42 (3H, s), 2.60-2.94 (11H, m), 3.35 (2H, t), 3.46 (3H, s), 6.81-6.86 (2H, m), 7.17-7.22 (1H, m).

Example 6

5-(5-(3-(5-fluoro-2,3-dihydrospiro[indene-1,3'-pyrrolidine]-1'-yl)propylthio)-4-methyl-4H-1,2,4-triazol-3-yl)-2,4-dimethylthiazole hydrochloride (E6)

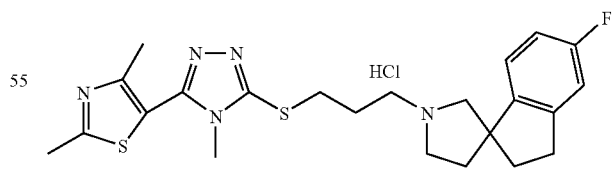

To a solution of 5-(5-(3-(5-fluoro-2,3-dihydrospiro[indene-1,3'-pyrrolidine]-1'-yl)propylthio)-4-methyl-4H-1,2,4-triazol-3-yl)-2,4-dimethylthiazole (Prep18, 38 mg) in a mixture of Et$_2$O (3 ml) and methanol (0.5 ml) was added 0.1 ml of HCl/Ether (1M in Et$_2$O), the solvent was evaporated in vacuo and treated with Et$_2$O (5 ml) to give 30 mg of the title compound (y=73%).

¹H NMR (MeOD) δ: 2.10-2.49 (6H, m), 2.50 (3H, s), 2.86 (3H, s), 2.98 (2H, m), 3.30-3.61 (6H, m), 3.71 (3H, s), 3.72-3.99 (2H, m), 6.90-7.06 (2H, m), 7.49-7.51 (1H, m).

Example 7

1-(4-(5-fluoro-2,3-dihydrospiro[indene-1,3'-pyrrolidine]-1'-yl)butyl)-5-(thiophen-2-yl)pyrimidine-2,4(1H,3H)-dione hydrochloride (E7)

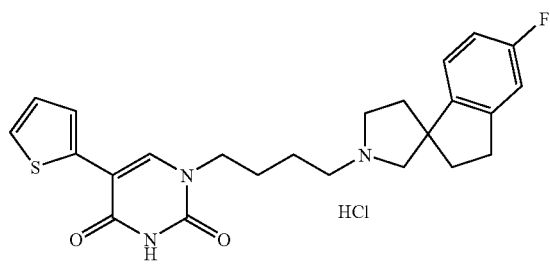

A mixture of 1-(4-chlorobutyl)-5-(thiophen-2-yl)pyrimidine-2,4(1H,3H)-dione (Prep23, 50 mg, 0.18 mmol), 5-fluoro-2,3-dihydrospiro[indene-1,3'-pyrrolidine]hydrochloride salt (Prep14, 50 mg, 0.26 mmol), potassium carbonate (108 mg, 0.78 mmol), sodium iodide (108 mg, 0.72 mmol) and NMP (1 ml) was stirred at 70° C. overnight. The mixture was then diluted with water and extracted with ethyl acetate. The EA phase was evaporated and the crude purified by preparative TLC to give the free base of the title compound (72 mg). The compound was purified by preparative HPLC and treated with a 1N solution of HCl-ether and freeze-dried to give the title compound (30 mg, y=35%).

¹H NMR (MeOD) δ: 1.70-1.98 (4H, m), 2.10-2.50 (4H, m), 2.98 (2H, t), 3.20-3.55 (4H, m), 3.70-4.00 (4H, m), 6.91-7.06 (3H, m), 7.31-7.46 (3H, m), 8.08 (1H, s). ES(MS) m/z 440 (MH+).

Example 8

1-(4-(5-chloro-2,3-dihydrospiro[indene-1,3'-pyrrolidine]-1'-yl)butyl)-5-(thiophen-2-yl)pyrimidine-2,4(1H,3H)-dione hydrochloride (E8)

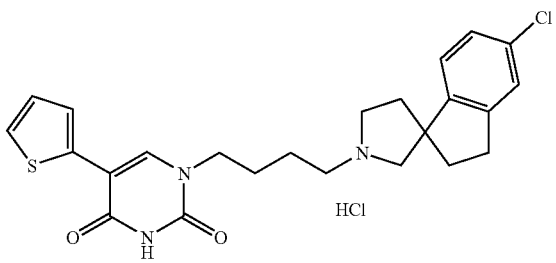

A mixture of 1-(4-chlorobutyl)-5-(thiophen-2-yl)pyrimidine-2,4(1H,3H)-dione (Prep23, 50 mg, 0.18 mmol), 5-chloro-2,3-dihydrospiro[indene-1,3'-pyrrolidine]hydrochloride (Prep10, 66 mg, 0.27 mmol), potassium carbonate (112 mg, 0.81 mmol), sodium iodide (108 mg, 0.72 mmol) and NMP (1 ml) was stirred at 70° C. overnight. Then it was cooled down to room temperature and diluted with water and extracted with ethyl acetate. The EA phase was evaporated and the crude purified by preparative TLC (TLC analysis performed by eluting with EA) to give the free base of the title compound (72 mg). The compound was purified by preparative HPLC and treated with a 1N solution of HCl-ether and freeze-dried give the title compound (51 mg, y=58%).

¹H NMR (MeOD) δ: 1.70-2.00 (4H, m), 2.15-2.50 (4H, m), 2.98 (2H, t), 3.20-3.55 (4H, m), 3.70-4.00 (4H, m), 7.03-7.06 (1H, m), 7.23-7.47 (5H, m), 8.10 (1H, s). ES(MS) m/z 456 (MH+).

Example 9

1-(3-(5-fluoro-2,3-dihydrospiro[indene-1,3'-pyrrolidine]-1'-yl)propyl)-5-(thiophen-2-yl)pyrimidine-2,4(1H,3H)-dione hydrochloride (E9)

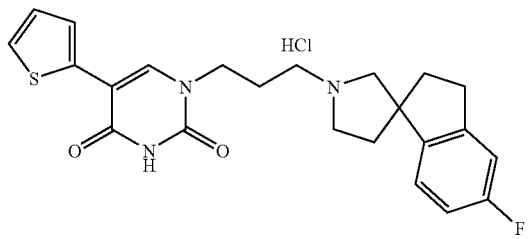

A mixture of 1-(3-chloropropyl)-5-(thiophen-2-yl)pyrimidine-2,4(1H,3H)-dione (Prep24, 50 mg, 0.18 mmol), 5-fluoro-2,3-dihydrospiro[indene-1,3'-pyrrolidine]hydrochloride salt (Prep14, 52 mg, 0.27 mmol), potassium carbonate (112 mg, 0.81 mmol), sodium iodide (112 mg, 0.75 mmol) and NMP (1 ml) was stirred at 70° C. overnight. The mixture was diluted with water and extracted with ethyl acetate. The EA phase was evaporated and the crude purified by preparative TLC to give the free base of the title compound (60 mg). the compound was purified by preparative HPLC and treated with a 1N solution of HCl-ether to give the title compound (6 mg, y=7%).

¹H NMR (MeOD) δ: 2.13-2.50 (6H, m), 2.98 (2H, m), 3.25-3.55 (4H, m), 3.71-4.05 (4H, m), 6.95-7.06 (3H, m), 7.34-7.38 (2H, m), 7.46-7.47 (1H, d), 8.10 (1H, s). ES(MS) m/z 426 (MH+).

Example 10

1-(3-(5-chloro-2,3-dihydrospiro[indene-1,3'-pyrrolidine]-1'-yl)propyl)-5-(thiophen-2-yl)pyrimidine-2,4(1H,3H)-dione hydrochloride (E10)

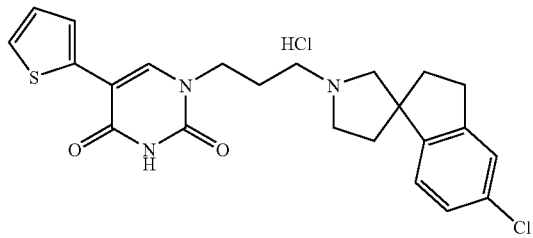

A mixture of 1-(3-chloropropyl)-5-(thiophen-2-yl)pyrimidine-2,4(1H,3H)-dione (Prep24, 50 mg, 0.18 mmol), -5-(thiophen-2-yl)pyrimidine-2,4(1H,3H)-dione (Prep24, 50 mg, 0.18 mmol), 5-chloro-2,3-dihydrospiro[indene-1,3'-pyrrolidine]hydrochloride salt (Prep10, 66 mg, 0.27 mmol), potassium carbonate (112 mg, 0.81 mmol), sodium iodide (112 mg, 0.75 mmol) and NMP (1 ml) was stirred at 70° C. overnight. Then it was cooled down to room temperature and diluted with water and extracted with ethyl acetate. The EA phase was evaporated and the crude purified by preparative TLC (TLC analysis performed by eluting with EA/MeOH 10:1) to give the free base of the title compound (70 mg). The compound was purified by preparative HPLC and treated with a 1N solution of HCl-ether to give the title compound (9 mg, y=10%).

$^1$H NMR (MeOD) δ: 2.15-2.50 (6H, m), 2.99 (2H, m), 3.25-3.55 (4H, m), 3.71-4.05 (4H, m), 7.05-7.06 (1H, m), 7.24-7.46 (5H, m), 8.09 (1H, s). ES(MS) m/z 442(MH$^+$).

The compounds in the following table (E11-E13) were prepared using an analogous procedure to that set out earlier in E7 starting from the appropriate spiro amine and the appropriate alkylating agent (in the table below):

| Ex. No | Spiro amine | Alk agent | Chemical name | Structure | NMR |
|---|---|---|---|---|---|
| E11 | Prep 4 | Prep 48 | 1-[3-(5-bromo-2,3-dihydro-1'H-spiro[indene-1,3'-pyrrolidin]-1'-yl)propyl]-5-methyl-2,4(1H,3H)-pyrimidinedione hydrochloride | 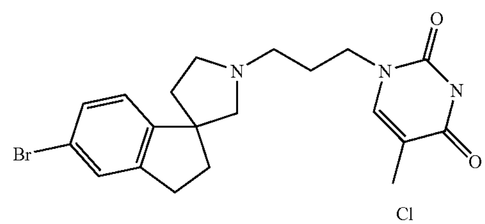 | $^1$H NMR (500 MHz, DMSO-d$_6$) δ ppm 11.27-11.34 (m, 1 H) 10.40 (br. s., 1 H) 7.49-7.58 (m, 1 H) 7.36-7.48 (m, 3 H) 3.61-3.80 (m, 4 H) 3.11-3.30 (m, 4 H) 2.84-2.92 (m, 2 H) 1.84-2.32 (m, 6 H) 1.71-1.80 (m, 3 H) |
| E12 | Prep 4 | Prep 49 | 1-[4-(5-bromo-2,3-dihydro-1'H-spiro[indene-1,3'-pyrrolidin]-1'-yl)butyl]-5-methyl-2,4(1H,3H)-pyrimidinedione hydrochloride | 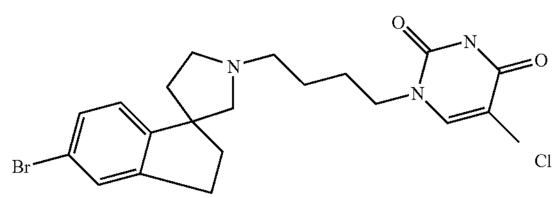 | $^1$H NMR (500 (MHz, DMSO-d$_6$) δ ppm 11.18-11.32 (m, 1 H) 10.54 (br. s., 1 H) 7.52-7.59 (m, 1 H) 7.33-7.49 (m, 3 H) 3.54-3.80 (m, 4 H) 3.02-3.36 (m, 4 H) 2.82-2.94 (m, 2 H) 1.84-2.34 (m, 4 H) 1.71-1.77 (m, 3 H) 1.54-1.75 (m, 4 H) |
| E13 | Prep 32 | Prep 50 | 1-[5-(6-bromo-3,4-dihydro-1'H,2H-spiro[naphthalene-1,3'-pyrrolidin]-1'-yl)pentyl]-5-methyl-2,4(1H,3H)-pyrimidinedione hydrochloride | 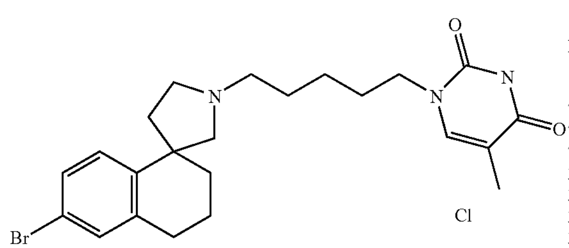 | $^1$H NMR (500 MHz, DMSO-d$_6$) δ ppm 11.20-11.25 (m, 1 H) 10.51 br. s., 1 H) 7.50-7.56 (m, 2 H) 7.37-7.42 (m, 1 H) 7.25-7.33 (m, 1 H) 3.66-3.74 (m, 2 H) 3.61-3.63 (m, 2 H) 3.29-3.40 (m, 1 H) 3.17-3.28 (m, 2 H) 3.10-3.17 (m, 1 H) 2.68-2.75 (m, 2 H) 2.01-2.38 (m, 2 H) 1.73-2.01 (m, 2 H) 1.73-1.75 (m, 3 H) 1.63-1.74 (m, 4 H) 1.53-1.64 (m, 2 H) 1.27-1.28 (m, 2 H) |

The compounds in the following table (E14-E21) were prepared using an analogous procedure to that set out earlier in E1 starting from the appropriate spiro amine (in the table below) and 3-[(3-chloropropyl)thio]-4-methyl-5-(4-methyl-1,3-oxazol-5-yl)-4H-1,2,4-triazole (reference procedure for preparation described in WO05/080382).

| Ex. No | Spiro amine | Chemical name | Structure | NMR |
|---|---|---|---|---|
| E14 | Prep 30 | 6-bromo-1'-(3-{[4-methyl-5-(4-methyl-1,3-oxazol-5-yl)-4H-1,2,4-triazol-3-yl]thio}propyl)-2,3-dihydrospiro[indene-1,3'-pyrrolidine]hydrochloride | 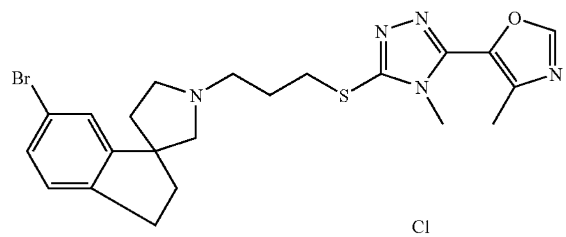 | $^1$H NMR (500 MHz, DMSO-d$_6$) δ ppm 10.47-10.76 (m, 1 H) 8.54-8.60 (m, 1 H) 7.65-7.76 (m, 1 H) 7.35-7.41 (m, 1 H) 7.18-7.23 (m, 1 H) 3.67-3.70 (m, 3 H) 3.66-3.92 (m, 2 H) 3.19-3.45 (m, 6 H) 2.79-2.88 (m, 2 H) 2.36-2.37 (m, 3 H) 1.89-2.39 (m, 6 H) |
| E15 | Prep 31 | 4-bromo-1'-(3-{[4-methyl-5-(4-methyl-1,3-oxazol-5-yl)-4H-1,2,4-triazol-3-yl]thio}propyl)-2,3-dihydrospiro[indene-1,3'-pyrrolidine]hydrochloride | 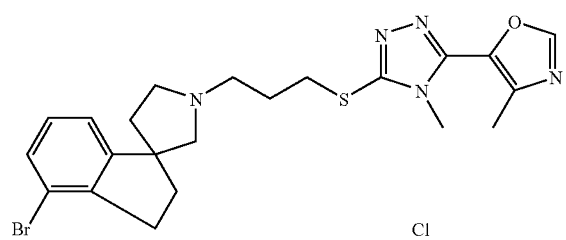 | $^1$H NMR (500 MHz, DMSO-d$_6$) δ ppm 10.67 (br. s., 1 H) 8.43-8.67 (m, 1 H) 7.39-7.51 (m, 2 H) 7.15-7.26 (m, 1 H) 3.64-3.72 (m, 3 H) 3.59-3.88 (m, 2 H) 3.10-3.53 (m, 6 H) 2.78-2.96 (m, 2 H) 2.32-2.40 (m, 3 H) 1.83-2.42 (m, 6 H) |
| E16 | Prep 32 | 6-bromo-1'-(3-{[4-methyl-5-(4-methyl-1,3-oxazol-5-yl)-4H-1,2,4-triazol-3-yl]thio}propyl)-3,4-dihydro-2H-spiro[naphthalene-1,3'-pyrrolidine]hydrochloride | 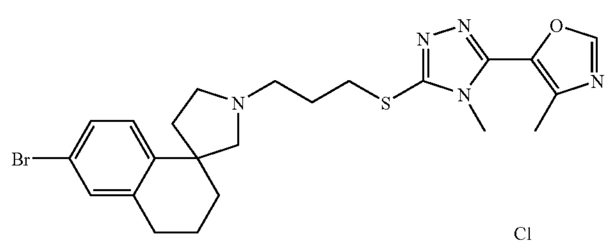 | $^1$H NMR (500 MHz, DMSO-d$_6$) δ ppm 10.44 (br. s., 1 H) 8.55-8.58 (m, 1 H) 7.56 (d, 1 H) 7.34-7.43 (m, 1 H) 7.29-7.32 (m, 1 H) 3.70-3.82 (m, 2 H) 3.65-3.71 (m, 3 H) 3.22-3.48 (m, 5 H) 3.10-3.21 (m, 1 H) 2.67-2.76 (m, 2 H) 2.32-2.41 (m, 4 H) 1.78-2.27 (m, 7 H) 1.64-1.76 (m, 2 H) |
| E17 | Prep 33 | 7-bromo-1'-(3-{[4-methyl-5-(4-methyl-1,3-oxazol-5-yl)-4H-1,2,4-triazol-3-yl]thio}propyl)-3,4-dihydro-2H-spiro[naphthalene-1,3'-pyrrolidine]hydrochloride | 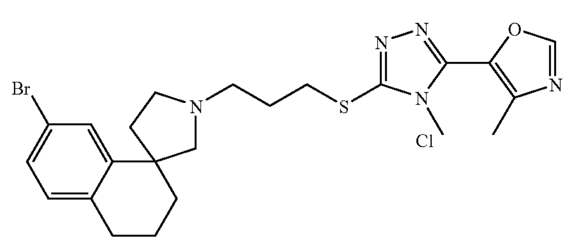 | $^1$H NMR (500 MHz, DMSO-d$_6$) δ ppm 10.48 (br. s., 1 H) 8.55-8.58 (m, 1 H) 7.80-7.89 (m, 1 H) 7.28-7.36 (m, 1 H) 7.00-7.08 (m, 1 H) 3.70-3.87 (m, 2 H) 3.67-3.70 (m, 3 H) 3.34-3.41 (m, 2 H) 3.25-3.32 (m, 2 H) 3.11-3.26 (m, 2 H) 2.67-2.68 (m, 2 H) 2.35-2.38 (m, 3 H) 2.34-2.44 (m, 1 H) 2.02-2.29 (m, 3 H) 1.63-2.03 (m, 4 H) |

| Ex. No | Spiro amine | Chemical name | Structure | NMR |
|---|---|---|---|---|
| E18 | Prep 35 | 1'-(3-{[4-methyl-5-(4-methyl-1,3-oxazol-5-yl)-4H-1,2,4-triazol-3-yl]thio}propyl)-7-(methyloxy)-3,4-dihydro-2H-spiro[naphthalene-1,3'-pyrrolidine]hydrochloride | 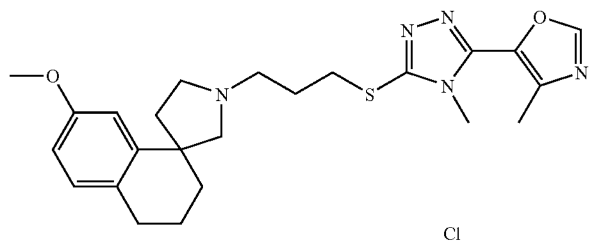 | $^1$H NMR (500 MHz, DMSO-d$_6$) δ ppm 10.12-11.03 (m, 1 H) 8.50-8.62 (m, 1 H) 7.04-7.28 (m, 1 H) 6.91-7.04 (m, 1 H) 6.66-6.82 (m, 1 H) 3.73-3.76 (m, 3 H) 3.69-3.87 (m, 2 H) 3.66-3.70 (m, 3 H) 3.23-3.51 (m, 5 H) 3.10-3.24 (m, 1 H) 2.59-2.68 (m, 2 H) 2.36-2.47 (m, 1 H) 2.34-2.37 (m, 3 H) 1.62-2.23 (m, 7 H) |
| E19 | Prep 34 | 1'-(3-{[4-methyl-5-(4-methyl-1,3-oxazol-5-yl)-4H-1,2,4-triazol-3-yl]thio}propyl)-6-(methyloxy)-3,4-dihydro-2H-spiro[naphthalene-1,3'-pyrrolidine]hydrochloride | 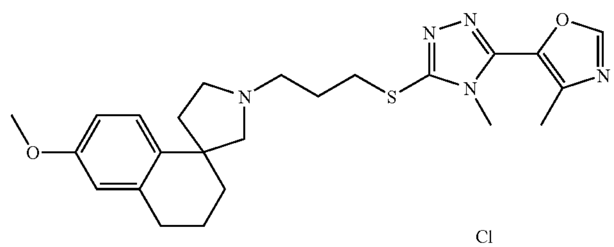 | $^1$H NMR (500 MHz, DMSO-d$_6$) δ ppm 10.34 (br. s., 1 H) 8.49-8.60 (m, 1 H) 7.48 (d, 1 H) 6.72-6.84 (m, 1 H) 6.54-6.65 (m, 1 H) 3.63-3.79 (m, 8 H) 3.05-3.50 (m, 6 H) 2.61-2.77 (m, 2 H) 2.32-2.40 (m, 3 H) 2.25-2.44 (m, 1 H) 2.08-2.22 (m, 2 H) 1.55-2.07 (m, 5 H) |
| E20 | Prep 36 | 1'-(3-{[4-methyl-5-(4-methyl-1,3-oxazol-5-yl)-4H-1,2,4-triazol-3-yl]thio}propyl)-5-(methyloxy)-3,4-dihydro-2H-spiro[naphthalene-1,3'-pyrrolidine]hydrochloride | 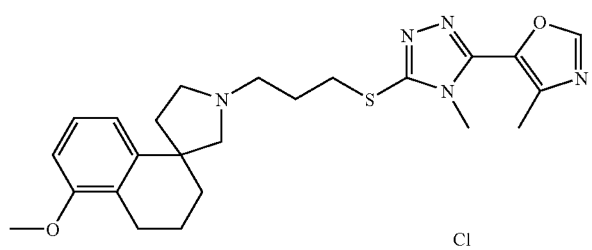 | $^1$H NMR (500 MHz, DMSO-d$_6$) δ ppm 10.54 (br. s., 1 H) 8.52-8.61 (m, 1 H) 7.11-7.29 (m, 2 H) 6.75-6.85 (m, 1 H) 3.74-3.75 (m, 3 H) 3.71-3.81 (m, 2 H) 3.66-3.70 (m, 3 H) 3.34-3.49 (m, 3 H) 3.24-3.32 (m, 2 H) 3.11-3.22 (m, 1 H) 2.56-2.65 (m, 1 H) 2.43-2.54 (m, 1 H) 2.35-2.37 (m, 3 H) 2.32-2.41 (m, 1 H) 2.09-2.25 (m, 2 H) 1.92-2.09 (m, 1 H) 1.60-1.92 (m, 4 H) |
| E21 | Prep 37 | 1'-(3-{[4-methyl-5-(4-methyl-1,3-oxazol-5-yl)-4H-1,2,4-triazol-3-yl]thio}propyl)-2,3-dihydrospiro[chromene-4,3'-pyrrolidine]hydrochloride | 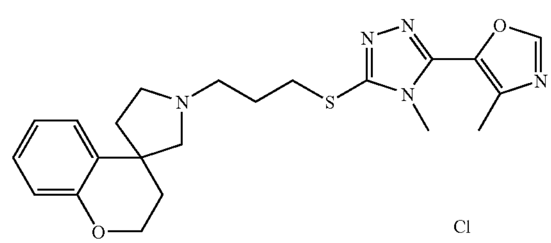 | $^1$H NMR (500 MHz, DMSO-d$_6$) δ ppm 10.60 (br. s., 1 H) 8.54-8.59 (m, 1 H) 7.53-7.61 (m, 1 H) 7.09-7.17 (m, 1 H) 6.91-6.97 (m, 1 H) 6.73-6.79 (m, 1 H) 4.07-4.21 (m, 2 H) 3.73-3.85 (m, 2 H) 3.66-3.70 (m, 3 H) 3.26-3.31 (m, 2 H) 3.22-3.50 (m, 4 H) 2.39-2.47 (m, 1 H) 2.35-2.38 (m, 3 H) 1.93-2.28 (m, 5 H) |

Example 22

5-(5-(3-(6-fluoro-2,3-dihydrospiro[indene-1,3'-pyrrolidine]-1'-yl)propylthio)-4-methyl-4H-1,2,4-triazol-3-yl)-2,4-dimethylthiazole hydrochloride (E22)

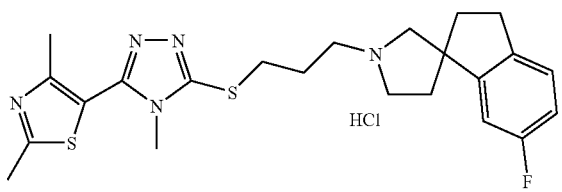

The mixture of 6-fluoro-2,3-dihydrospiro[indene-1,3'-pyrrolidine] (Prep43, 95 mg, 0.45 mmol), K$_2$CO$_3$ (137 mg, 1 mmol), NaI (100 mg, 0.6 mmol), and 5-(5-(3-chloropropylthio)-4-methyl-4H-1,2,4-triazol-3-yl)-2,4-dimethylthiazole (Prep28, 100 mg, 0.3 mmol) in NMP (2 ml) was warmed to 70° C. The mixture was stirred at 70° C. for 72. The mixture was extracted with EA. The organic phase was concentrated in vacuo and the crude was purified by P-TLC (TLC analysis performed by eluting with EA/MeOH 90:10) followed by P-HPLC. The free base of the title compound was then treated with a 1N solution of HCl/ether to obtain the title compound (13.2 mg, y=8.7%).

$^1$H NMR (MeOD) δ: 7.19-7.24 (2H, m), 6.92-6.94 (1H, m), 3.73-3.95 (2H, m), 3.66 (3H, s), 3.30-3.60 (6H, m), 2.90-2.93 (2H, m), 2.82 (3H, s), 2.47 (3H, s), 2.00-2.45 (6H, m).

ES(MS) m/z 458 (MH$^+$).

HPLC: 96.55%.

Example 23

5-(5-(3-(6-chloro-2,3-dihydrospiro[indene-1,3'-pyrrolidine]-1'-yl)propylthio)-4-methyl-4H-1,2,4-triazol-3-yl)-2,4-dimethylthiazole hydrochloride (E23)

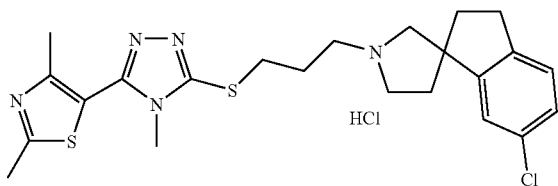

The mixture of 6-chloro-2,3-dihydrospiro[indene-1,3'-pyrrolidine] (Prep47, 100 mg, 0.37 mmol), K$_2$CO$_3$ (110 mg, 0.8 mmol), sodium iodide (80 mg, 0.53 mmol), and 5-(5-(3-chloropropylthio)-4-methyl-4H-1,2,4-triazol-3-yl)-2,4-dimethylthiazole (Prep28, 80 mg, 0.28 mmol) in NMP (4 ml) was warmed to 70° C. The mixture was stirred at 70° C. overnight. The mixture diluted with water (20 ml), extracted with EA (10 ml). The organic layers were combined and washed with Sat. NaHCO$_3$, Sat. brine and dried over anhydrous Na$_2$SO$_4$. The organics was evaporated under vacuum to get crude product. The crude product was purified by P-TLC (TLC analysis performed by eluting with PE/EA 1:1), then P-HPLC. The free base of the compound was then converted into the title compound (treatment with 1 eq of 1N HCl) and dried under vacuum to give the desired product as white solid (20 mg, y=11.4%).

$^1$H NMR (MeOD) δ: 7.38-7.43 (1H, m), 7.16-7.17 (2H, m), 3.75-3.91 (2H, m), 3.69-3.74 (1H, m), 3.55-3.58 (3H, m), 3.32-3.48 (5H, m), 2.88-2.91 (2H, m), 2.75-2.83 (3H, s), 2.30-2.49 (6H, m).

ES(MS) m/z 474 (MH$^+$).

HPLC: 98.32%.

All publications, including but not limited to patents and patent applications, cited in this specification are herein incorporated by reference as if each individual publication were specifically and individually indicated to be incorporated by reference herein as though fully set forth.

It is to be understood that the present invention covers all combinations of particular groups described herein above.

The application of which this description and claims forms part may be used as a basis for priority in respect of any subsequent application. The claims of such subsequent application may be directed to any feature or combination of features described herein. They may take the form of product, composition, process, or use claims and may include, by way of example and without limitation, the following claims:

The invention claimed is:

1. A compound of formula (I) or a salt thereof:

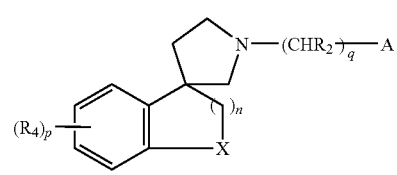

wherein

A is P, P1, P2 or P3 wherein

P is

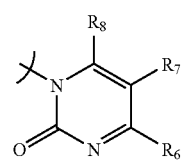

P1 is

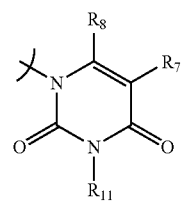

P2 is and

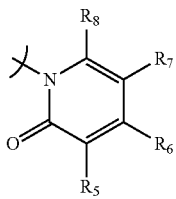

P3 is

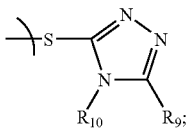

p is an integer ranging from 0 to 4;
$R_4$ is halogen, hydroxy, cyano, $C_{1-4}$alkyl, halo$C_{1-4}$alkyl, $C_{1-4}$alkoxy, halo$C_{1-4}$alkoxy, $C_{1-4}$alkanoyl, $SF_5$ or a 5- or 6-membered monocyclic heteroaryl group; wherein when p is an integer ranging from 2 to 4, each $R_4$ may be the same or different;
$R_2$ is hydrogen or $C_{1-4}$alkyl;
q is 3, 4 or 5;
n is 0, 1 or 2;
X is —$CR_1R_3$— or —O—;
$R_1$ is hydrogen, $C_{1-4}$alkyl or fluorine;
$R_3$ is hydrogen, $C_{1-4}$alkyl or fluorine;
$R_5$ is hydrogen, halogen, hydroxy, cyano, $C_{1-4}$alkyl, $C_{3-7}$cycloalkyl, halo$C_{1-4}$-alkyl, $C_{1-4}$alkoxy, halo$C_{1-4}$alkoxy, $C_{1-4}$alkanoyl and NR'R''; or $R_5$ is a phenyl group, or a 5-14 membered heterocyclic group; wherein the phenyl or heterocyclic group is optionally substituted by 1, 2, 3 or 4 substituents which is halogen, cyano, $C_{1-4}$alkyl, halo$C_{1-4}$alkyl, $C_{1-4}$-alkoxy, $C_{1-4}$alkanoyl or $SF_5$;
$R_6$ is hydrogen, halogen, hydroxy, cyano, $C_{1-4}$alkyl, $C_{3-7}$cycloalkyl, halo$C_{1-4}$alkyl, $C_{1-4}$alkoxy, halo$C_{1-4}$alkoxy, $C_{1-4}$alkanoyl or NR'R''; or $R_6$ is a phenyl group, a 5-14 membered heterocyclic group, wherein the phenyl or heterocyclic group is optionally substituted by 1, 2, 3 or 4 substituents which is halogen, cyano, $C_{1-4}$alkyl, halo$C_{1-4}$alkyl, $C_{1-4}$alkoxy, $C_{1-4}$alkanoyl or $SF_5$;
$R_7$ is hydrogen, halogen, hydroxy, cyano, $C_{1-4}$alkyl, $C_{3-7}$cycloalkyl, halo$C_{1-4}$-alkyl, $C_{1-4}$alkoxy, halo$C_{1-4}$alkoxy, $C_{1-4}$alkanoyl or NR'R''; or $R_7$ is a phenyl group, a 5-14 membered heterocyclic group; wherein the phenyl or heterocyclic group is optionally substituted by 1, 2, 3 or 4 substituents which is halogen, cyano, $C_{1-4}$alkyl, halo$C_{1-4}$alkyl, $C_{1-4}$alkoxy, $C_{1-4}$alkanoyl or $SF_5$;
$R_8$ is hydrogen, halogen, hydroxy, cyano, $C_{1-4}$alkyl, $C_{3-7}$cycloalkyl, halo$C_{1-4}$alkyl, $C_{1-4}$alkoxy, halo$C_{1-4}$alkoxy, $C_{1-4}$alkanoyl or NR'R''; or $R_8$ is a phenyl group, a 5-14 membered heterocyclic group; wherein the phenyl or heterocyclic group is optionally substituted by 1, 2, 3 or 4 substituents which is halogen, cyano, $C_{1-4}$alkyl, halo$C_{1-4}$alkyl, $C_{1-4}$alkoxy, $C_{1-4}$alkanoyl or $SF_5$;
$R_9$ is hydrogen, a phenyl group, a heterocyclyl group, a 5- or 6-membered monocyclic heteroaryl group, or a 8- to 11-membered heteroaryl bicyclic, wherein any group is optionally substituted by 1, 2, 3 or 4 substituents selected from the group consisting of: halogen, cyano, $C_{1-4}$alkyl, halo$C_{1-4}$alkyl, $C_{1-4}$alkoxy and $C_{1-4}$alkanoyl;
$R_{10}$ is $C_{1-4}$alkyl;
$R_{11}$ is hydrogen or $C_{1-4}$alkyl;
R' is H, $C_{1-4}$ alkyl or $C_{1-4}$alkanoyl;
R'' is the same as R';
R' and R'' taken together with the interconnecting nitrogen atom may form a 5-, 6-membered saturated or unsaturated heterocyclic ring;
wherein $R_5$, $R_6$, $R_7$ and $R_8$ are not simultaneously other than hydrogen; and wherein only one $R_2$ group may be different from hydrogen and wherein when n is 0, X is a group —$CR_1R_3$—.

2. A compound as claimed in claim 1 which is a compound of formula (IA)

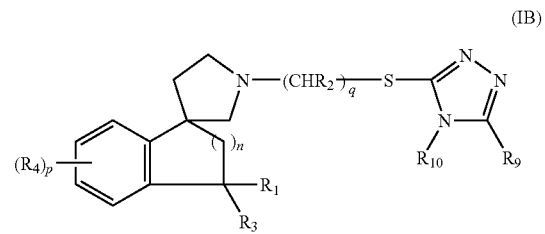

or a salt thereof, wherein $R_1$, $R_2$, $R_3$, $R_4$, $R_9$, $R_{10}$, p, q, n, $R_7$, $R_{11}$ and $R_8$ are as defined for formula (I).

3. A compound as claimed in claim 1 which is a compound of formula (IB)

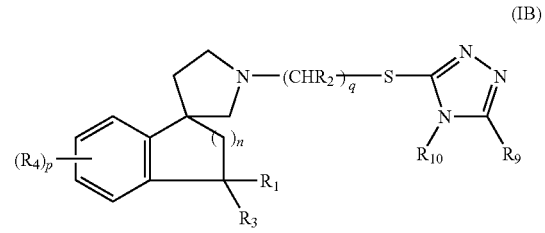

or a salt thereof, wherein $R_4$ and n are as defined for compounds of formula (I).

4. A compound of formula (I), as claimed in claim 1, selected in the group consisting of:
5-bromo-1'-(3-{[3-(4-methyl-1,3-oxazol-5-yl)-1H-1,2,4-triazol-5-yl]thio}propyl)-2,3-dihydrospiro[indene-1,3'-pyrrolidine];
5-(5-(3-(5-chloro-6-methoxy-2,3-dihydrospiro[indene-1,3'-pyrrolidine]-1'-yl)propylthio)-4-methyl-4H-1,2,4-triazol-3-yl)-2,4-dimethylthiazole;
5-(5-(3-(5-chloro-2,3-dihydrospiro[indene-1,3'-pyrrolidine]-1'-yl)propylthio)-4-methyl-4H-1,2,4-triazol-3-yl)-2,4-dimethylthiazole;
5-(5-(3-(5-chloro-2,3-dihydrospiro[indene-1,3'-pyrrolidine]-1'-yl)propylthio)-4-methyl-4H-1,2,4-triazol-3-yl)-2,4-dimethylthiazole;
5-(5-(3-(5-fluoro-2,3-dihydrospiro[indene-1,3'-pyrrolidine]-1'-yl)propylthio)-4-methyl-4H-1,2,4-triazol-3-yl)-2,4-dimethylthiazole;
5-(5-(3-(5-fluoro-2,3-dihydrospiro[indene-1,3'-pyrrolidine]-1'-yl)propylthio)-4-methyl-4H-1,2,4-triazol-3-yl)-2,4-dimethylthiazole;

1-(4-(5-fluoro-2,3-dihydrospiro[indene-1,3'-pyrrolidine]-1'-yl)butyl)-5-(thiophen-2-yl)pyrimidine-2,4(1H,3H)-dione;

1-(4-(5-chloro-2,3-dihydrospiro[indene-1,3'-pyrrolidine]-1'-yl)butyl)-5-(thiophen-2-yl)pyrimidine-2,4(1H,3H)-dione;

1-(3-(5-fluoro-2,3-dihydrospiro[indene-1,3'-pyrrolidine]-1'-yl)propyl)-5-(thiophen-2-yl)pyrimidine-2,4(1H,3H)-dione hydrochloride;

1-(3-(5-chloro-2,3-dihydrospiro[indene-1,3'-pyrrolidine]-1'-yl)propyl)-5-(thiophen-2-yl)pyrimidine-2,4(1H,3H)-dione;

1-[3-(5-bromo-2,3-dihydro-1'H-spiro[indene-1,3'-pyrrolidin]-1'-yl)propyl]-5-methyl-2,4(1H,3H)-pyrimidinedione;

1-[4-(5-bromo-2,3-dihydro-1'H-spiro[indene-1,3'-pyrrolidin]-1]-yl)butyl]-5-methyl-2,4(1H,3H)-pyrimidinedione;

1-[5-(6-bromo-3,4-dihydro-1'H,2H-spiro[naphthalene-1,3'-pyrrolidin]-1'-yl)pentyl]-5-methyl-2,4(1H,3H)-pyrimidinedione;

6-bromo-1'-(3-{[4-methyl-5-(4-methyl-1,3-oxazol-5-yl)-4H-1,2,4-triazol-3-yl]thio}propyl)-2,3-dihydrospiro[indene-1,3'-pyrrolidine];

4-bromo-1'-(3-{[4-methyl-5-(4-methyl-1,3-oxazol-5-yl)-4H-1,2,4-triazol-3-yl]thio}propyl)-2,3-dihydrospiro[indene-1,3'-pyrrolidine];

6-bromo-1'-(3-{[4-methyl-5-(4-methyl-1,3-oxazol-5-yl)-4H-1,2,4-triazol-3-yl]thio}propyl)-3,4-dihydro-2H-spiro[naphthalene-1,3'-pyrrolidine];

7-bromo-1'-(3-{[4-methyl-5-(4-methyl-1,3-oxazol-5-yl)-4H-1,2,4-triazol-3-yl]thio}propyl)-3,4-dihydro-2H-spiro[naphthalene-1,3'-pyrrolidine];

1'-(3-{[4-methyl-5-(4-methyl-1,3-oxazol-5-yl)-4H-1,2,4-triazol-3-yl]thio}propyl)-7-(methyloxy)-3,4-dihydro-2H-spiro[naphthalene-1,3'-pyrrolidine];

1'-(3-{[4-methyl-5-(4-methyl-1,3-oxazol-5-yl)-4H-1,2,4-triazol-3-yl]thio}propyl)-6-(methyloxy)-3,4-dihydro-2H-spiro[naphthalene-1,3'-pyrrolidine];

1'-(3-{[4-methyl-5-(4-methyl-1,3-oxazol-5-yl)-4H-1,2,4-triazol-3-yl]thio}propyl)-5-(methyloxy)-3,4-dihydro-2H-spiro[naphthalene-1,3'-pyrrolidine];

1,3-oxazol-5-yl)-4H-1,2,4-triazol-3-yl]thio}propyl)-2,3-dihydrospiro[chromene-4,3'-pyrrolidine];

5-(5-(3-(6-fluoro-2,3-dihydrospiro[indene-1,3'-pyrrolidine]-1'-yl)propylthio)-4-methyl-4H-1,2,4-triazol-3-yl)-2,4-dimethylthiazole;

5-(5-(3-(6-chloro-2,3-dihydrospiro[indene-1,3'-pyrrolidine]-1'-yl)propylthio)-4-methyl-4H-1,2,4-triazol-3-yl)-2,4-dimethylthiazole;

or a salt thereof.

5. A pharmaceutical composition comprising a compound as claimed in claim 1 or a pharmaceutically acceptable salt thereof, in association with a pharmaceutically acceptable carrier.

\* \* \* \* \*